(12) United States Patent
Duan et al.

(10) Patent No.: US 9,556,247 B2
(45) Date of Patent: Jan. 31, 2017

(54) STABILIZED AMYLOID-BETA OLIGOMERS AND USES THEREOF

(75) Inventors: Roxanne Duan, Bethesda, MD (US); Jonathan Moll, Rockville, MD (US); Alan S. Rudolph, Potomac, MD (US)

(73) Assignee: SYSTEM OF SYSTEMS ANALYTICS, INC., Fairfax, VA (US)

( * ) Notice: Subject to any disclaimer, the term of this patent is extended or adjusted under 35 U.S.C. 154(b) by 491 days.

(21) Appl. No.: 13/698,857

(22) PCT Filed: May 24, 2011

(86) PCT No.: PCT/US2011/037711
§ 371 (c)(1),
(2), (4) Date: Jul. 3, 2013

(87) PCT Pub. No.: WO2011/149917
PCT Pub. Date: Dec. 1, 2011

(65) Prior Publication Data
US 2013/0274437 A1    Oct. 17, 2013

Related U.S. Application Data

(60) Provisional application No. 61/396,378, filed on May 25, 2010, provisional application No. 61/348,186, filed on May 25, 2010.

(51) Int. Cl.
  *C07K 14/47*  (2006.01)
  *C07K 1/14*   (2006.01)
(52) U.S. Cl.
  CPC ............. *C07K 14/4711* (2013.01); *C07K 1/14* (2013.01)
(58) Field of Classification Search
  CPC .................................................. C07K 14/4711
  See application file for complete search history.

(56) References Cited

U.S. PATENT DOCUMENTS

| 7,166,471 | B2 | 1/2007 | Orser et al. | |
|---|---|---|---|---|
| 7,691,639 | B2 | 4/2010 | Orser et al. | |
| 8,062,895 | B2 | 11/2011 | Orser et al. | |
| 8,372,593 | B2 | 2/2013 | Orser et al. | |
| 8,673,579 | B2 | 3/2014 | Orser et al. | |
| 2006/0134754 | A1* | 6/2006 | Chan ...................... | C07K 14/54 435/69.52 |

OTHER PUBLICATIONS

Danielsson et al. (Biochemistry 2004, 43, 6261-6269).*
U.S. Appl. No. 14/445,846, filed Jul. 29, 2014, Wegrzyn et al.
U.S. Appl. No. 14/484,683, filed Sep. 12, 2014, Orser et al.
U.S. Appl. No. 14/299,432, filed Jun. 9, 2014, Duan et al.
U.S. Appl. No. 14/584,560, filed Dec. 29, 2014, Duan et al.
U.S. Appl. No. 14/296,721, filed Jun. 5, 2014, Deuerstein et al.
Huang et al., "Structural Studies of Soluble Oligomers of the Alzheimer β-Amyloid Peptide," J. Mol. Biol., vol. 297, pp. 73-87, 2000.
Mastrangelo et al., "High-resolution atomic force microscopy of soluble Abeta42 oligomers," J. Mol. Biol., vol. 358, No. 1, pp. 106-0119.
International Search Report issued on Oct. 31, 2011 in application No. PCT/US2011/37711.

* cited by examiner

*Primary Examiner* — Amber D Steele
(74) *Attorney, Agent, or Firm* — Foley & Lardner LLP

(57) ABSTRACT

The present invention pertains to stabilized Aβ oligomer compositions. Methods for generating stabilized Aβ oligomer compounds are also provided herein. Additionally, screening assays employing the Aβ oligomer compounds and methods for generating therapeutics with the Aβ oligomers are also provided. In a particular embodiment, the Aβ oligomer described herein is comprised of Aβ42 peptide.

20 Claims, 10 Drawing Sheets

Figure 2    SDS-PAGE gels of AB42 SDS oligomers. we plan on making F12 lanes a separate figure Figure 3 SEC profiles for several lots of AB42 SDS oligomers Figure 4  Results from liquid stability testing of AB42 SDS oligomer, each inset will be separate figure The data show that only AB42 SDS and F12 oligomers cause a substantial change in the fluorescence profile of the Pronucleon peptide as indicated by the increase in the fluorescence response. AB40 and 42 monomers and fiber, as well as unrelated proteins BSA and CA, have little or no effect on the fluorescence profile of the peptide.

STABILIZED AMYLOID-BETA OLIGOMERS AND USES THEREOF

RELATED APPLICATIONS

This application claims the benefit of priority to U.S. provisional application 61/396,378, filed May 25, 2010 and U.S. provisional application 61/348,186, filed May 25, 2010, the entire contents of which are incorporated herein by reference in their entirety.

FIELD OF THE INVENTION

The present invention relates to compositions comprising stabilized soluble amyloid-β (Aβ) oligomer peptides. The stabilized Aβ oligomer containing compositions are useful in screening assays for agents that interact with Aβ oligomers or for agents that enhance or inhibit oligomer formation, thereby aiding in the development of AD therapeutic agents. Additionally, stabilized Aβ oligomers are useful in the development of diagnostic assays for the detection of Alzheimer Disease (AD), and as control reagents in such assays.

BACKGROUND OF THE INVENTION

Alzheimer's disease (AD), a degenerative and incurable form of dementia, has been correlated with the accumulation of neurofibrillary tangles and amyloid plaques/fibrils, the latter of which are neurotoxic, and comprise Aβ peptide subunits (WO 2007/005359)(Klein et al, 2004, Neur. Biol. Aging 25 (5):569-580). Aβ peptides are typically 39-43 amino acids in length, and are produced by endoproteolysis of the amyloid-β precursor protein (APP) (Bitan et al. (2001) *JBC* 276 35176-35184). Studies have shown that Aβ42 is the most common monomer subunit found in Aβ plaques of Alheimer's patients (Sanders et al. (2009). *Peptides* 30, 849-854). Additionally, elevated plasma levels of Aβ42 have been associated with AD (see U.S. 2008/0095706); and increased Aβ42/40 ratios in cerebrospinal fluid (CSF) have been correlated with increased risk of progression from Mild Cognitive Impairment (MCI) to AD (Brys M et al, 2009, Neur. Biol. Aging 30 (5): 682-690.

Under pathological conditions, Aβ peptides undergo conformational changes, from nascent random coil structures to β-sheet conformations (WO 2008/028939). The β-sheet conformation is stabilized by intermolecular hydrogen bonds between individual β-sheets. Conversion to the β-sheet conformation leads to stacking of β-sheets, creating Aβ oligomers and eventually fibrils. Mechanistic studies of Aβ fibril formation suggest that certain soluble assemblies of Aβ, including Aβ oligomers, are intermediates in fibril formation. Additionally, it has been found that the Aβ oligomers are metastable and form spontaneously at low concentrations of Aβ peptide (Lambert et al. (1998). *PNAS* 95 6448-6453).

Although formation of Aβ fibrils is a pathological feature of AD, the number and distribution of Aβ fibrils and plaques do not always correlate with neurodegeneration or clinical dementia (Dahlgren et al. (2002). *JBC*, 277 32046-32053). It is therefore unclear whether the accumulation of Aβ fibrils is associated with causation of AD, or is a late-stage manifestation of the disease. Recent evidence has shown that soluble assemblies of Aβ, such as oligomeric assemblies, amyloid-derived diffusible ligands (ADDLs) and Aβ protofibrils, are neurotoxic elements, suggesting a pathological role for Aβ that has not assembled into fibrils.

There are many examples in the AD literature demonstrating that endogenous Aβ oligomers are an important toxic species in AD. For example, Aβ oligomers present in untreated ex vivo human CSF has been shown to rapidly and potently disrupt synaptic plasiticity mechanisms that are believed to underlie memory in the hippocampal network, whereas isolated Aβ monomers had no such effect (Klyubin et al., 2008, J. Neuroscience, 28 (16): 4231-4237). Moreover, soluble Aβ oligomers isolated from AD brains have been shown to disrupt the memory of learned behavior in normal rats (Shankar et al., 2008, Nature Medicine, epub). Studies of multiple strains of APP-transgenic mice show synapse loss, in the absence of fibrillar amyloid deposits, that correlates with levels of Aβ immunoreactivity in soluble extracts (Mucke et al., 2000, J. Neuroscience 20:4050; Lauren et al., 2009, Nature 457: 1128-1132). These findings, however, do not rule out an additional or distinct pathological role for Aβ fibers in development of AD (Kirkitadze et al. (2001). *JMB* 312 1103-1119; WO 2006/004824).

Synthetically produced oligomers have been shown to have effects similar to those described for naturally occurring oligomers. For example, Aβ42 ADDL's, formed in F12 media, have been shown to specifically inhibit hippocampal long-term potentiation (but don't effect cerebellar neurons) when administered at sub-micromolar doses, and are correlated with synapse loss, effects similar to the activity described for naturally-occuring oligomers in the previous paragraph (Klein, 2002, Neurochemistry Int., 41: 345-352; Klein et al, 2001, Trends Neuroscience, 24:219-224). SDS-derived Aβ42 oligomers also demonstrate specific effects on LTP of hippocampal tissue, as well specifically interacting with dendritic processes of hippocampal neurons (Barghorn et al, 2005, J. Neurochemistry, 95: 834-847).

Aβ monomers and oligomers, including oligomers comprised of Aβ42, are inherently thermodynamically unstable, making it difficult to use the same oligomer composition over an extended period of time. Due to the Aβ peptide's hydrophobic nature, it is favorable for the Aβ peptide to form higher order structures. Accordingly, Aβ peptides form high molecular weight fibrils that readily precipitate from aqueous solution. Although soluble Aβ oligomers have been studied with regard to their neurotoxicity, these studies have been hindered due to the tendency of oligomers to aggregate or combine to form higher order structures.

In an attempt to circumvent the problem of Aβ aggregation, Aβ oligomers are typically stored precipitated or solubilized in PBS or weakly buffered solutions and stored either at 4° C. or frozen. However, precipitated and frozen preparations are typically suitable for short-term usage only, due to their tendency to further aggregate and change their oligomeric characteristics. A stable composition of Aβ oligomers would be useful because it would allow work to be performed on Aβ oligomers without making repeated fresh preparations of oligomer; and reduce variability in oligomer preparations used in a series of investigations. The present invention addresses this and other needs.

SUMMARY OF THE INVENTION

The present invention is directed to compositions comprising stabilized Aβ oligomers and methods for making such compositions. The compositions can comprise soluble Aβ oligomers, i.e., covalent or noncovalent complexes comprising several to several hundred monomer units. The monomer units can be, but are not limited to, Aβ3-42, Aβ37, Aβ38, Aβ39, Aβ340 and Aβ42 monomers, or combinations thereof. In certain embodiments, stabilized Aβ oligomer compositions comprise Aβ oligomers in a buffer of sodium phosphate, glycine and a disaccharide. In these embodiments, the composition maintains a substantially stable percentage of soluble Aβ oligomers for a defined period of time. In a preferred embodiment, the composition has no detectable Aβ fibril component as determined by ThT staining. In another embodiment, the invention provides stabilized Aβ oligomer compositions with little or no Aβ fibril content (as determined by ThT staining), sodium phosphate, glycine and a disaccharide, is in the form of a solution. In a further embodiment, the disaccharide can be either sucrose or trehalose.

In one embodiment, the invention provides Aβ oligomer compositions that maintain substantially the same percentage of soluble Aβ oligomers for a period of time. In certain embodiments, Aβ oligomers are stable for 15-30 days (as a liquid at 4° C.), or 6-9 months as a lyophilized powder. In preferred embodiments, the oligomer content is expected to range from 70-95%, and the monomer content from 5-30% (as determined by size-exclusion chromatography under native conditions).

In another embodiment, the invention provides a method for preparing a stabilized Aβ oligomer composition. The method comprises forming Aβ oligomer solution from Aβ monomer peptides by incubation with 0.1 to 1% SDS and, as formed, being substantially free of precipitate; dialyzing said Aβ oligomer solution against a solution comprising a stabilizing amount of a disaccharide to form a disaccharide-stabilized Aβ oligomer solution containing trace amounts of SDS; and removing any Aβ fibers that have formed prior to completion of said dialyzing step to form said stabilized Aβ oligomer composition that maintains substantially the same percentage of soluble Aβ oligomers for a period of time 15-30 days at 4° C. (liquid formulation).

In another embodiment, the invention provides an alternative method for preparing a stabilized Aβ oligomer composition. The method comprises forming a DMEM/F12-Aβ oligomer solution comprising Aβ monomer peptide and equal parts DMEM and F12, that is substantially free of precipitate; dialyzing the F12-Aβ oligomer solution against a solution comprising a stabilizing amount of a disaccharide to form a disaccharide stabilized Aβ oligomer solution, wherein the Aβ oligomers in the solution are soluble; and removing any Aβ fibers that have formed prior to completion of said dialyzing step to form said stabilized Aβ oligomer composition that maintains substantially the same percentage of soluble Aβ oligomers for a period of time comprising 15-30 days at 4° C. (liquid formulation).

DETAILED DESCRIPTION OF THE INVENTION

Figure 1:
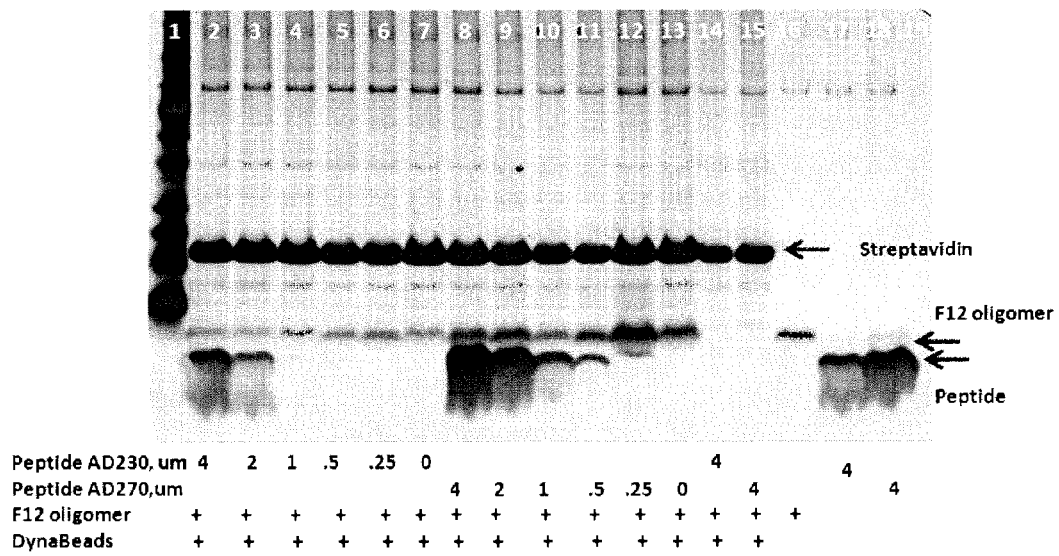
FIG. 1 is an image of a silver stained SDS-PAGE gel showing binding of two Pronucleon™ peptides to a biotinylated F12 Aβ oligomer.

Both Aβ oligomer and Aβ fibrils of Aβ peptide are correlated with the progression of AD. The precise mechanism by which Aβ exerts its toxicity, however, is unknown, despite more than 200 studies on Aβ neurotoxicity (see, e.g., U.S. Pat. No. 6,218,506). Soluble non-fibrillar Aβ species comprising two or more Aβ subunits have been reported to be neurotoxic in patients with AD. These findings suggest that agents which merely dissociate fibrils into smaller soluble species may be of limited or no therapeutic value, and that targeting the Aβ oligomeric intermediates may enhance therapeutic value. At the very least, the study of the oligomeric intermediates is a prerequisite to understanding Aβ-based toxicity and is anticipated to be useful in screening therapeutic agents for utility in the treatment of AD.

It is clear from the Aβ literature that reproducibility of results is problematic in both Aβ fibril and oligomer studies, probably due in large part, to differences among batches of Aβ monomer, starting material for making oligomers and fibrils, and to differences in protocols for preparing the oligomer and fibril compositions. Additionally, as mentioned above, apart from differences in oligomer composition and/or preparative protocol, Aβ oligomers are inherently unstable because of the thermodynamically driven tendency for oligomers to form highly ordered fibril structures.

Accordingly, the field of AD research stands to benefit from the development of an Aβ oligomer reagent that exhibits reproducible, stable physical characteristics over an extended period of time. The stability of the reagent would allow for a greater variety of experiments to be conducted which would investigate the mechanism of AD, for example time course experiments with the same batch of reagent. Prior to the present invention, the instability of Aβ oligomer required that Aβ oligomer reagents be prepared fresh, with each use. As described herein, this has led to more variability and less reproducibility in Aβ-related experiments.

DEFINITIONS

As used herein:

"Amyloid β (Aβ) peptide," refers to any or all Aβ peptides, including, for example and without limitation, Aβ3-42, Aβ37, Aβ38, Aβ39, Aβ40 and Aβ42 peptides, all known allelic variants and mutated forms of Aβ, e.g., Aβ mutations at amino acid residues 1 and 2 of the native sequence. See WO 02/094985 and WO 04/099376 for examples of peptides having modifications at amino acid residues 1 and 2 of the native Aβ sequence. Additional Aβ peptide point mutations include, without limitation, mutations at positions asn1, asn7, asn23, gly21, lys22, gly22, gln22, gln6, gln13, glyn14. See, e.g., Kirkitadze et al. (2001). *JMB* 312 1103-1119.

"Aβ oligomer" refers to a soluble association of two or more Aβ monomers (i.e., soluble Aβ multimers). Monomers may be associated either covalently or non-covalently (e.g., by covalent bonds, hydrogen bonds, ionic bonds, van der Waals interactions). "Aβ oligomers" include, but are not limited to, for example, soluble Aβ peptide dimers, trimers, tetramers, pentamers and hexamers, and dodecamers. "Aβ oligomers" may comprise one or more distinct Aβ peptide variants per oligomer. For example, an "Aβ oligomer" may include, for example, one, two, three, four, five, six, seven, eight, nine or ten distinct Aβ peptide variants. An acceptable oligomer solution can be defined as any aggregate comprised of Aβ monomer subunits that is soluble (no visible particulate matter by visual inspection), contains no appreciable fibrillar particles (as determined by ThT staining), and is recognized as being composed of ≥70% oligomer as determined by native SEC.

"Aβ fibril" and "Aβ fiber" are synonymous, and refer to an insoluble aggregate comprising Aβ monomer subunits that have highly ordered beta sheet structure and form fiber-like morphology when examined by microscopy; or that are ThT-sensitive.

A "stabilized Aβ oligomer composition" is a composition that comprises soluble Aβ oligomers and which maintains substantially the same percentage of soluble Aβ oligomers over a period of time. Preferably, a stabilized Aβ oligomer composition comprises substantially the same percentage of Aβ oligomers for at least 24 hours, more preferably for at least 15 days, and most preferably, at least 30 days. The percentage of Aβ oligomers and fibers in a composition can be determined, for example, by size exclusion chromatography. Other assays for determining the components of the stabilized Aβ oligomer composition are provided herein. The term "stabilized Aβ oligomer composition" encompasses dynamically stable compositions in which the total percentage of soluble complex is the same but the amounts of monomer and/or insoluble complex (i.e., fibril) vary.

"Soluble" means remaining in true aqueous solution.

"PDG buffer" refers to a buffer containing sodium phosphate, glycine and one or more disaccharides. In one embodiment, the PDG buffer contains 10 mM sodium phosphate, pH 7.4, 1.9% glycine and 40 mM-300 mM total disaccharide.

"PSG buffer" refers to a buffer containing sodium phosphate, glycine and sucrose. In one embodiment, the PSG buffer contains 10 mM sodium phosphate, pH 7.4, 1.9% glycine and 10 mM-300 mM sucrose.

"MWCO" refers to the molecular weight cut off of a filter, e.g., an ultrafiltration filter.

"Subject" refers to an experimental animal (e.g., mouse, rat, rabbit, dog and cat).

"Effective amount," or "effective dose" refers to an amount of a stabilized Aβ oligomer sufficient to result in a desired response. The response can be, for example, fluorescence generated from an MPD or ThT reaction, discussed in detail below. Alternatively or additionally, the response can be a behavioral response, e.g., a response to spatial memory tasks such as the Morris Water Maze and the Radial Arm Maze, described in Bryan et al. (2009). "Transgenic Mouse Models of Alzheimer's Disease: Behavioral Testing and Consideration, in *Methods of Behavior Analysis in Neuroscience*. 2d edition, Taylor and Francis Group. It is further within the skill of one of ordinary skill in the art to determine appropriate doses, based upon an evaluation of response.

"About," as used herein, refers to ±10% of a given value.

"Substantially the same" as "X" (or equivalent expressions of substantial identity or invariance) means a result that varies no more than 15% from "X". In the case of a fluorescence reaction, such as a ThT assay, 15% refers to the amount of fluorescence emitted in a ThT reaction.

Aβ Compositions

In certain aspects, the present invention is directed to compositions comprising stabilized soluble Aβ oligomers. Stabilized, soluble Aβ oligomers may be prepared from any species of Aβ monomer, for example, and without limitation, the species Aβ39, Aβ3-42, Aβ40 and Aβ42, and combinations thereof. Other Aβ peptides suitable for use with the present invention are described above. The oligomers can be homogeneous or heterogeneous in terms of its Aβ monomer content and number of monomer units combined into each oligomer complex. At a minimum, Aβ oligomers contain one monomer species and two monomer units. Alternatively, Aβ oligomers contain, for example and without limitation, two Aβ monomer species, three Aβ monomer species, four Aβ monomer species, five Aβ monomer species, six Aβ monomer species, twelve Aβ monomer species, or more.

Soluble Aβ oligomers comprise at least 2 monomer subunits and can comprise up to 1,000 monomer subunits. In one embodiment, the soluble Aβ oligomer compositions include at least 100 monomer subunits, at least 200 monomer subunits or at least 500 monomer subunits.

Without being bound by theory, stabilization occurs through the use of (i.e., transfer of the soluble oligomers in) a formulation buffer comprised of sodium phosphate, glycine and one or more disaccharides, as described in more detail below.

In one embodiment, an oligomer composition is obtained from Aβ42 monomer starting material. In another embodiment, a stabilized oligomer composition is obtained from Aβ40 monomer starting material. In yet another embodiment, the stabilized oligomer preparation is obtained from a mixture of Aβ42 and Aβ40 monomer starting material. In still another embodiment Aβ39 monomer is used as the starting material for oligomer preparation.

In another embodiment, the stabilized oligomer preparation contains a homogenous mixture of Aβ37 or Aβ38 monomer starting material. In still another embodiment, the oligomer preparation contains a heterogeneous mixture of Aβ monomers, and includes Aβ37 and/or Aβ38 monomer starting material.

Other embodiments include a stabilized oligomer preparation comprising Aβ3-42 monomer starting material.

In one embodiment, the Aβ oligomers are prepared in an SDS buffer, discussed below, and have a molecular weight of 4 kDa to 85 kDa. In another embodiment, the stabilized Aβ oligomers are prepared in F12 medium and have a molecular weight of 4 kDa to about 840 kDa. Still, other embodiments include Aβ oligomer preparations having a MW of 8 kDa to 250,000 kDa. Thus, oligomers may contain, for example and without limitation, a small number (e.g., 2, 3, 4, 5, 6, 7, 8, 9, 10 or so) of Aβ monomer units, and up to approximately 100,000 Aβ units.

The oligomer preparation methods described herein typically yield oligomer compositions with 20-30% monomers and 70-80% oligomers, and negligible fiber content (as determined by ThT); or 5-20% monomer, 80-95% oligomers, and negligible fiber content (F-12 derived oligomers.

SDS-Glutaraldehyde Crosslinked Aβ Oligomers

Aβ42 monomer as an HFIP film is solubilized in DMSO (e.g. 0.5 mg Aβ42+22 uL DMSO). 1×PBS and SDS are then added to make a solution of 100 uM Aβ42 and 0.2% SDS. This solution is incubated at 37 C for 24 hours. The sample is then centrifuged at 3000×g for 20 minutes to remove any fibrils. Gluteraldehyde is added to a final concentration of 0.01%, and incubated for 2 hours at room temperature. The crosslinking reaction is quenched by addition of ethanolamine at a final concentration of 0.03%, followed by incubation for 30 minutes at room temperature. The sample is then concentrated, and dialyzed into a stabilizing formulation buffer.

Functionalized Aβ Oligomers

In some instances, functionalized Aβ oligomers may be of use, for example, in oligomer binding assays, to determine whether one or more small molecules or peptidic molecules, such as antibodies, bind soluble Aβ oligomers. For example, soluble Aβ oligomers functionalized with biotin can be mixed with test compounds to determine whether one or more test compounds (e.g., in a compound library) bind to the oligomers. Then, the biotinylated Aβ oligomers can be isolated from the reaction mixture by introducing beads or another solid phase derivatized with avidin or streptavidin. Unbound material can then be washed away. Agents that bind the soluble Aβ oligomer compositions can then be precisely identified by methods known to those of ordinary skill in the biochemical and molecular biology arts.

Accordingly, in certain embodiments, the invention provides a stabilized Aβ oligomer composition comprising oligomers that have at least one biotin functional group attached to an Aβ monomer peptide. Commercially available biotinylated Aβ peptide monomer can be mixed in an appropriate ratio with one or more unlabeled Aβ monomer of the same or a different type. This mixture can then be incubated in a PBS/SDS solution (SDS-derived oligomers), or in F12:DMEM media to facilitate oligomer production. One of ordinary skill in the art can determine the optimal ratio of labeled to unlabeled Aβ monomer to ensure that subsequently produced oligomers have at least one biotin moiety per oligomer. In one embodiment, a 1:10 mol:mol ratio of labeled Aβ monomer to unlabeled Aβ monomer (also suspended in DMSO), is used to produce F12- or SDS-derived oligomers as per the standard protocol. The stabilized soluble oligomer composition can then be prepared as described below.

Alternatively or additionally, the stabilized Aβ oligomers can be labeled with a fluorescent tag/label, i.e., a fluorophore. A fluorescent label is useful because it can provide a quantitative readout mechanism in an Aβ oligomer binding assay. For example, an oligomer binding assay can be developed based on Fluorescence resonance energy transfer (FRET). In one FRET embodiment, a potential binding agent(s) is labeled with a donor fluorophore and the Aβ oligomer is labeled with an acceptor fluorophore. The donor fluorophore can then be excited at the appropriate wavelength, and if in close enough proximity to the acceptor fluorophore, transfer energy to the acceptor fluorophore. The acceptor fluorophore will then emit light according to an emission spectrum, specific for the respective acceptor fluorophore. The acceptor fluorophore will not fluoresce if it is not in close proximity to the donor fluorophore because it will not be in its excited state, as the excitation spectrum of the donor fluorophore is distinct from the excitation spectrum of the acceptor fluorophore.

In some instances, it may be useful to use a fluorescently labeled oligomer that is tagged with biotin. Biotinylation of a fluorescently labeled oligomer allows for isolation of the oligomer and any agent that interacts with it, before a readout step. If the oligomer is not isolated before fluorescent readout, false positives may be detected.

In one embodiment, fluorescently labeled oligomer is detected by using a non FRET fluorescence reaction. For example, oligomer bound to a fluorescent label can be reacted with biotin labeled target molecules, to determine whether binding occurs. The complex can be sequestered or isolated with streptavidin, and fluorescence measured. The amount of fluorescence emitted is directly correlated with oligomer binding.

In one embodiment, Aβ peptide monomer is labeled with fluorescein. Other fluorophores that can be used to label Aβ peptides are given below. A fluorophore can be chosen according to the particular assay and the desired wavelength for fluorescence excitation and emission. For example, and without limitation, Aβ peptide monomer can be fluorescently labeled and suspended in DMSO, and mixed in an appropriate ratio with unlabeled Aβ monomer. One of ordinary skill in the art can determine the optimal ratio for fluorescent labeling the Aβ monomer. In a preferred embodiment, a 1:10 mol:mol ratio of labeled Aβ monomer to unlabeled Aβ monomer (also suspended in DMSO), is used. The soluble oligomer composition can then be prepared as described below.

Where preferred, Aβ monomer may be both biotinylated and labeled with a fluorophore. Aβ monomer is first biotinylated and labeled with a fluorophore, and then reconstituted in DMSO, as described in detail above. Dual-labeled monomer may be mixed in a 1:10 mol:mol ratio with unlabeled Aβ monomer (suspended in DMSO), followed by the processing steps described below, to arrive at a stabilized oligomer.

Fluorescent labels (fluorophores) amenable for labeling Aβ peptides, present as either monomer or in Aβ complexes, include compounds with a fluorescent emission maximum between about 350 and 900 nm. A wide variety of fluorophores can be used, including, without limitation: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein; ([4,7,2',4',5'-hexachloro-(3',6'-dipivaloyl-fluoresceinyl)-6-carboxylic acid]); 6-Hexachloro-Fluorescein; ([4,7,2',4',5',7'-hexachloro-(3',6'-dipivaloylfluoresceinyl)-5-carboxylic acid]); 5-Tetrachloro-Fluorescein; ([4,7,2',7'-tetra-chloro-(3',6'-dipivaloylfluoresceinyl)-5-carboxylic acid]); 6-Tetrachloro-Fluorescein; ([4,7,2',7'-tetrachloro-(3',6'-dipivaloylfluoresceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS (5-((2-aminoethyl)

amino)naphthalene-1-sulfonic acid); 1,5-IAEDANS (5-((((2-iodoacetyl)amino)ethyl)amino)naphthalene-1-sulfonic acid); Cy5 (Indodicarbocyanine-5); Cy3 (Indo-dicarbocyanine-3); and BODIPY FL (2,6-dibromo-4,4-difluoro-5,7-dimethyl-4-bora-3a,4a-diaza-s-indacene-3-proprionic acid); Quasar-670 (Biosearch Technologies); CalOrange (Biosearch Technologies); Rox (rhodamine derivative), as well as suitable derivatives thereof.

When desired, different Aβ monomer species (e.g., Aβ40 and/or Aβ42) can be labeled with fluorophores that exhibit unique emission spectra. Multiplexing with distinct fluorophores allows for the study of self-assembly of heterogeneous Aβ oligomers. The molecular composition of the Aβ oligomer can then be determined by measuring the fluorescence emission of the distinct fluorophores. Multiplexing also allows for the identification and study of agents that bind to distinct oligomer types.

A non-limiting list of representative homogenous and heterogeneous Aβ oligomers that can be stabilized in compositions and methods described herein is given in Table 1.

PDG buffer may include various concentrations of disaccharide. An appropriate disaccharide concentration depends on the Aβ concentration present in the material after the sample has been oligomerized and concentrated by ultrafiltration. A sufficiently high molar ratio of the stabilizing disaccharide to Aβ oligomer must be present to form a uniform glassy matrix, and to adequately maintain essential hydrogen bonding interactions upon lyophilization. The appropriate disaccharide: Aβ oligomer ratio may be determined empirically in stability studies for particular oligomer compositions and concentrations using methods known in the art. PDG buffer may include, for example and without limitation, disaccharide ranges from 1 mM to 400 mM. In certain embodiments, the concentration of the disaccharide is selected from 1 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, 300 mM, 310 mM, 320 mM, 330 mM, 340 mM, 350 mM, 360 mM, 370 mM, 380 mM, 390 mM and 400 mM.

TABLE 1

| Aβ39 oligomers | Aβ40 oligomers | Aβ42 oligomers | Aβ40/Aβ42 oligomers | Aβ3-42 oligomers | Aβ39/Aβ42 oligomers |
|---|---|---|---|---|---|
| SDS Aβ39 | SDS Aβ40 | SDS Aβ42 | SDS Aβ40/Aβ42 | SDS Aβ3-42 | SDS Aβ39/Aβ42 |
| Biotinylated SDS Aβ39 | Biotinylated SDS Aβ40 | Biotinylated SDS Aβ42 | Biotinylated SDS Aβ40/Aβ42 | Biotinylated SDS Aβ3-42 | Biotinylated SDS Aβ39/Aβ42 |
| Fluorescein labeled SDS Aβ39 | Fluorescein labeled SDS Aβ40 | Fluorescein labeled SDS Aβ42 | Fluorescein labeled SDS Aβ40/Aβ42 | Fluorescein labeled SDS Aβ3-42 | Fluorescein labeled SDS Aβ39/Aβ42 |
| Biotinylated Fluorescein labeled SDS Aβ39 | Biotinylated Fluorescein labeled SDS Aβ40 | Biotinylated Fluorescein labeled SDS Aβ42 | Biotinylated Fluorescein labeled SDS Aβ40/Aβ42 | Biotinylated Fluorescein labeled SDS Aβ3-42 | Biotinylated Fluorescein labeled SDS Aβ39/Aβ42 |
| F12 Aβ39 | F12 Aβ40 | F12 Aβ42 | F12 Aβ40/Aβ42 | F12 Aβ3-42 | F12 Aβ39/Aβ42 |
| Biotinylated F12 Aβ39 | Biotinylated F12 Aβ40 | Biotinylated F12 Aβ42 | Biotinylated F12 Aβ40/Aβ42 | Biotinylated F12 Aβ3-42 | Biotinylated F12 Aβ39/Aβ42 |
| Fluorescein labeled F12 Aβ39 | Fluorescein labeled F12 Aβ40 | Fluorescein labeled F12 Aβ42 | Fluorescein labeled F12 Aβ40/Aβ42 | Fluorescein labeled F12 Aβ3-42 | Fluorescein labeled F12 Aβ39/Aβ42 |
| Biotinylated Fluorescein labeled F12 Aβ39 | Biotinylated Fluorescein labeled F12 Aβ40 | Biotinylated Fluorescein labeled F12 Aβ42 | Biotinylated Fluorescein labeled F12 Aβ40/Aβ42 | Biotinylated Fluorescein labeled F12 Aβ3-42 | Biotinylated Fluorescein labeled F12 Aβ39/Aβ42 |
| Disulfide-linked Aβ39 Dimer | Disulfide-linked Aβ40 Dimer | Disulfide-linked Aβ42 Dimer | Disulfide-linked Aβ40/Aβ42 Dimer | Disulfide-linked Aβ3-42 Dimer | Disulfide-linked Aβ39/Aβ42 Dimer |
| Biotinylated Disulfide-linked Aβ39 Dimer | Biotinylated Disulfide-linked Aβ40 Dimer | Biotinylated Disulfide-linked Aβ42 Dimer | Biotinylated Disulfide-linked Aβ40/Aβ42 Dimer | Biotinylated Disulfide-linked Aβ3-42 Dimer | Biotinylated Disulfide-linked Aβ39/Aβ42 Dimer |
| SDS-glutaraldehyde crosslinked Aβ39 | SDS-glutaraldehyde crosslinked Aβ40 | SDS-glutaraldehyde crosslinked Aβ42 | SDS-glutaraldehyde crosslinked Aβ40/Aβ42 | SDS-glutaraldehyde crosslinked Aβ3-42 | SDS-glutaraldehyde crosslinked Aβ39/Aβ42 |

Stabilization of Aβ Oligomers

Stabilization of soluble Aβ oligomer compositions may be effected using a PDG buffer, i.e., a buffer containing sodium phosphate, glycine, and a non-reducing disaccharide. Preferred disaccharides are sucrose and trehalose. In a more preferred embodiment, the disaccharide is sucrose.

Without wishing to be bound by theory, the primary stabilization agent in the PDG buffer is believed to be the disaccharide, e.g., sucrose. It is thought that the disaccharide may stabilize the oligomers by providing a glassy matrix of high viscosity that inhibits protein unfolding. Alternatively or additionally, the disaccharide may act as a replacement for water in hydrogen bonding interactions that may be essential for maintenance of a stable oligomer secondary structure.

A preferred disaccharide for use in PDG buffer is sucrose. A PDG buffer with sucrose as the disaccharide is referred to throughout as a PSG buffer. PSG buffer preferably and without limitation, contains a sucrose concentration selected from 300 mM and 40 mM sucrose. PSG buffer can also include sucrose concentration ranges from 1 mM to 400 mM.

Sodium phosphate is used in both the PDG and PSG buffers. Typically, the concentration and pH of the sodium phosphate are 10 mM and pH 7.4, respectively. However, other concentrations and pHs of sodium phosphate that may be used in PDG and PSG buffers are, for example, and without limitation, 5-100 mM $NaH_2PO_4$; pH 5-8. One of ordinary skill in the art will readily know how to adjust the pH of sodium phosphate, e.g., by mixing precalculated amounts of monobasic and dibasic sodium phosphate. For example, sodium phosphate, pH 7 is prepared by mixing 39% monobasic sodium phosphate with 61% dibasic sodium phosphate. Sodium phosphate is primarily used as a buffering agent to maintain pH at the preferred value. Other buffering agents with pH ranges from 4-10 can be used (e.g., HEPES, Bis-Tris Propane, Tris, Histidine, etc).

Glycine is also used in both the PDG and PSG buffers. PDG and PSG buffers may include, for example and without limitation, 1.9% glycine or about 1.9% glycine. The percentage of glycine in the PDG and PSG buffers preferably ranges from 0.5%-5%. Without being bound by theory, glycine is believed to act as both a bulking agent (to provide a consistent lyophilized powder that can be easily solubilized); and as a cryoprotectant. Other cryorotectants can also be used in the present invention, for example, mannitol.

The PDG and PSG buffer may optionally contain polysorbate 20, commonly known as Tween20, available commercially. The percentage of Tween20 in the PDG or PSG buffer typically ranges from 0.001%-0.1%, e.g., 0.01%.

The oligomers can remain stable in both lyophilized and reconstituted forms. Typically, reconstituted oligomers are prepared by suspending the lyophilized oligomer in water such that the concentrations of the individual formulation components are retained.

Additional Aβ Oligomer Stabilization Reagents

Antioxidants

Aβ oligomers contain multiple methionine residues that may be subject to oxidation, that could in turn result in decreased stability. Antioxidants (e.g., ascorbic acid) may be used to minimize oxidative degradation of this type. Antioxidants are typically used at very low concentrations from 0.001% to 0.2%, if needed.

Nonionic Detergents

Nonionic detergents (for example, polysorbate20 or 80 (Tween20 or Tween80)), are often used in protein formulations to protect products from aggregation at air-water and water-surface interfaces, by reducing their effective concentrations at these interfaces. Moreover, these detergents may specifically reduce or prevent aggregation of hydrophobic proteins such as Aβ oligomers in liquids by reducing oligomer:oligomer interactions. Such excipients may be useful in extending the stability lifetime of Aβ oligomers currently used (i.e., F12- and SDS-derived Aβ42 oligomers).

Aβ Oligomer Characterization

Once a stabilized Aβ oligomer preparation has been made, it can be characterized in a number of ways. For example, a lyophilized sample can be reconstituted and visually inspected to determine if any particulate matter is present. Particulate matter implies the presence of impurities, notably fibrils. Preferably, stabilized Aβ oligomer compositions exhibit no particulate upon visual inspection.

The components (wherein all the soluble, oligomeric species are considered as one component) of the reconstituted stabilized soluble Aβ oligomer composition can be determined by polyacrylamide gel electrophoresis (PAGE), e.g., by SDS-PAGE, wherein components of the oligomer preparation are separated according to electrophoretic mobility, which is a function of MW. Components separated in gels can then be visualized by staining using methods well known in the art. This method can be used to quantitate any change in the monomer content or specific oligomers bands, as well as characterize the overall size profile of the oligomer preparation.

Aβ oligomers can also be characterized by their ability to bind to Thioflavin T (ThT), a reagent that specifically interacts with the crossed-β-pleated sheet structure common to Aβ fibrils (Kudva et al. (1998). *Biochem. J.* 331, 809-813). ThT fluoresces upon interaction with Aβ fibrils, but does not fluoresce in the presence of other forms of Aβ. An increase in fluorescence in this assay is directly correlated with the presence and formation of Aβ fibrils. Accordingly, an oligomer composition that exhibits increased ThT fluorescence over time is indicative of Aβ fibril formation, and therefore, an unstable Aβ oligomer composition.

In one example of a ThT binding assay, stabilized Aβ oligomer preparations are subjected to a ThT reaction at various time points, and exhibit substantially the same fluorescence at all time points tested. The time points may be taken at 0 days and 1 day. Alternatively, time points are taken at 0 days, 1 day and 2 days; 0 days, 1 day, 2, days, 7 days, 14 days and 33 days; 1 week, 2 weeks and 3 weeks; 1 week, 2 weeks, 3 weeks, 4 weeks 6 weeks and 8 weeks; or 1 week, 2 weeks, 3 weeks, 4 weeks, 6 weeks, 8 weeks and 12 weeks. By comparison, unstabilized Aβ oligomer compositions begin deteriorating as soon as they are formed, and therefore, do not exhibit substantially the same fluorescence in a ThT reaction, at various time points. As used herein, "0 days" refers to the time immediately after formation of the Aβ composition is complete.

Chromatography experiments can also be employed to determine the purity and makeup of an Aβ oligomer preparation. An Aβ oligomer sample can be subjected to size exclusion chromatography (SEC) at various time points to determine if the oligomer structure remains, if it dissociates into monomers. This determination is made by looking at the sharpness of the peaks, and the peak locations in the respective spectra.

A consistent profile over days, weeks and/or months indicates that the same sample can be used to develop diagnostic or therapeutic assays over that time period. This leads to more reproducible results, as no variability is added by making new oligomer preparations.

The stability of the Aβ oligomer compositions can also be determined by electron microscopy, using techniques well known in the art. Oligomer compositions may be subjected to electron microscopy at time point 0 (i.e., 0 days), and at least one other time point, e.g., 1 day, 2 days, 7 days, 14 days, etc. The stability of the composition is determined by comparing electron micrographs at the time points. If substantially more fibrils (i.e., at least 10% more) are visually discernable at the time point(s), as compared to 0 days, the composition is not deemed to be a stable oligomer composition.

The two most direct means to determine the oligomeric state of the oligomers presented herein, and to monitor changes in oligomeric state over time, are size-exclusion chromatography (SEC) and SDS-PAGE. Other possible methods include capillary gel electrophoresis (CGE) under either native or denaturing conditions.

Misfolded Protein Diagnostic (MPD) Assay

Figure 9:
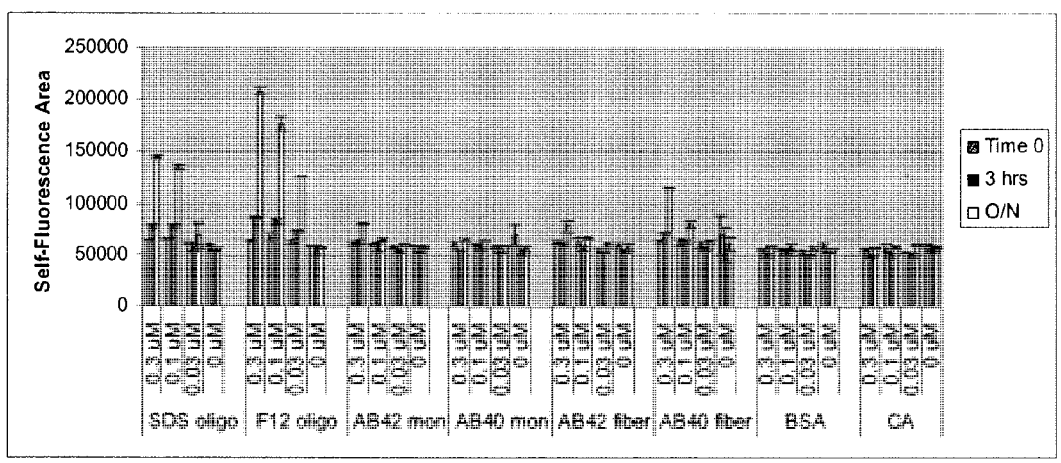
FIG. 9 shows MPD results for Aβ42 oligomers compared to monomer and fibril preparations.

The MPD assay exploits the basis of misfolded protein disease—protein conformational change from α-helix to β-sheet. A fluorescent peptide, typically pyrenated ALZ peptide 22 or pyrenated Pronucleon™ peptide, is combined with the oligomer preparations described herein. If the respective peptide binds the oligomer composition, the peptide can undergo a conformational change resulting in changes to the peptide's fluorescence emission profile. This fluorescence profile change is not seen when peptide is incubated either with Aβ monomer or fibril (For example, see FIG. 9). Therefore, the MPD assay can quantify the amount of Aβ oligomer in a sample by measuring pyrene fluorescence. Additionally, if an oligomer composition is subjected to this assay at various time points (e.g., at 0 days, 1 day and 7 days), it can give an indication of Aβ fibril formation over time, and therefore, the stability and fidelity of the composition over time.

Methods for Preparing Stabilized Aβ Oligomer Compositions

General Aβ Monomer Preparation

Aβ monomer, as described above, can be commercially obtained or synthesized by known peptide synthesis procedures. Monomer is typically lyophilized and dissolved in a solvent, preferably a polar aprotic solvent, such as dimethyl sulfoxide (DMSO). The amount of solvent used for dissolving the Aβ monomer is dependent on the amount of monomer starting material. For example, in one embodiment, 1.0 mg of monomer starting material is dissolved in 40 μL-50 μL solvent. Alternatively, the amount of DMSO used to dilute the lyophilized monomer can be 40, 41, 42, 43, 44, 45, 46, 47, 48, 49, 50, 51, 52, 53, 54 or 55 μL.

To speed dissolution of the Aβ monomers, the monomer suspension can be sonicated. Sonication times and power required to solubilize Aβ monomers may be varied by one of ordinary skill in the art, and are both a function of the amount of monomer starting material and solvent used to initially dissolve the monomer. Sonication times include, for example, 5 seconds, 10 seconds, 15 seconds, 20 seconds, 25 seconds and 30 seconds. Power wattage for sonication may be selected from 5 Watts (W), 10 W, 15 W, 16 W, 17 W, 18 W, 19 W, 20 W, 21 W, 22 W, 23 W, 24 W, 25 W, 26 W, 27 W, 28 W, 29 W and 30 W. Optimal combinations of sonication time and power can be readily determined by one of ordinary skill in the art.

Optionally, after sonication, the Aβ monomer solution can be vortexed to create a homogeneous solution. In one embodiment, the sample is vortexed until a spiral flow of the solution is visually observed. For example, the monomer solution can be vortexed for 2, 3, 4 or 5 seconds; and up to including 30 seconds at 1 second intervals.

The monomer solution can be diluted further in phosphate-buffered saline (1×PBS). The amount of 1×PBS added to the monomer solution depends on both the amount of solvent originally used to dissolve the monomer, and the concentration of the monomer starting material. 1.5 mL-2.5 mL 1×PBS can be added to the monomer solution, e.g., 2 mL 1×PBS is added to the Aβ monomer solution.

Aβ Oligomer Preparation with SDS

Sodium dodecyl sulfate (SDS) can be used to facilitate the formation of Aβ oligomers from the monomer starting material. As with the amount of solvent and 1×PBS used in the monomer preparation, the percentage of SDS, and the amount of SDS solution used depends on the amount of Aβ monomer starting material, and the makeup of the material (i.e., the monomer species, see table 1 for examples). For example, 100-200 μL of a 2% SDS solution can be added to a solution that contained 1.0 mg monomer starting material. This amount can be scaled up or down by one of ordinary skill in the art, depending on the desired final concentration of SDS, and the amount of monomer starting material.

The SDS solution can consist of from 0.06%-1% SDS. For example, 2% SDS can be employed to facilitate the formation of Aβ oligomers from Aβ monomers. In another embodiment, 0.06%, 0.1%, 0.3%, 0.5%, 0.7%, or 1% SDS solution can be added to the PBS-monomer mixture.

F12 Oligomer Preparation

DMEM/F12 (1:1) (no phenol red) can then be added to the homogenous monomer solution to facilitate Aβ oligomer formation. Typically, about 1 mL to about 4 mL of the cell culture medium is added to 1.0 mg of Aβ monomer. The volume of cell culture medium used is dependent on the amount of Aβ starting material. The volume of medium added can be readily varied and optimized by one of ordinary skill in the art. In one embodiment, 2.2 mL or about 2.2 mL of the cell culture medium is added to the monomer solution. The mixture is subsequently vortexed to ensure a homogenous solution. For example, the solution can be vortexed for about 5 seconds to about 30 seconds. In one embodiment, the mixture is vortexed for about 15, about 20, about 25 or about 30 seconds. In a further embodiment, the vortex step is for 30 seconds.

To further facilitate Aβ oligomer formation, the resulting SDS or F12 oligomer mixture can be incubated at 37° C. for a set period of time, typically 16-48 hours. However, this time can be optimized by one of ordinary skill in the art. The solution can then be vortexed, as described above, to ensure the homogeneity of the Aβ oligomer solution.

Although SDS and DMEM/F12 both facilitate the formation of Aβ oligomers from Aβ monomers, Aβ fibrils may also form. The fibrils should preferably be removed before any further processing. For example, fibrils can be removed by centrifugation, filtration, or chromatography. For example, the SDS oligomer mixture described above can be aliquoted into appropriate tubes and centrifuged.

Centrifugation can be employed to pellet any Aβ fibrils and/or debris that may be present in the Aβ oligomer solution. The time and force it takes to pellet Aβ fibrils/debris depends on the amount of fibrils/debris present in the oligomer solution, and can be varied by one of ordinary skill in the art. For example, centrifugation at 3000×g for 20 minutes is typically sufficient to pellet Aβ fibrils, when starting with 1.0 mg Aβ monomers. Centrifugation step may also be carried out for a longer period of time at a lower g force. After centrifugation, Aβ fibrils present in the mixture will be pelleted out of solution. The supernatants are then used for further processing.

Alternatively, the oligomer solution may be centrifuged at 4° C. to remove any Aβ fibrils that may be present. The centrifugation tubes used depend on the compatibility of the centrifuge used, and can be readily determined by one of ordinary skill in the art. Centrifugation can be carried out at 14,000×g for 10 minutes at 4° C. Alternatively, the centrifugation step can be carried out for a longer period of time at a lower sample acceleration (i.e., lower g force). After centrifugation, Aβ fibrils present in the mixture are pelleted out of solution. The supernatants are then used for further processing.

The supernatants from the centrifugation step, or the SDS oligomer solution that has not been subjected to centrifugation can be processed through an ultrafiltration device to eliminate any high molecular weight particles in the solution. In one embodiment, the MWCO of the ultrafiltration device is 30 kDa.

The filtered sample can then be concentrated by ultrafiltration. Typically, the sample is concentrated at least 5 fold for optimal downstream processing. However, one of ordinary skill in the art can vary the centrifugation time and force to make a more concentrated or less concentrated oligomer solution. Centrifugation at 1500×g for 5-10 minutes is typically sufficient to concentrate the sample. Sample is centrifuged, e.g., for 5, 6, 7, 8, 9 or 10 minutes, or up to 20 minutes by 1 minute increments. Sample can also be centrifuged for a longer period of time if the g force is reduced.

Stabilization of the Aβ Oligomer Solutions

Following formation of the Aβ oligomer solution, the solution can be stabilized by dialyzing against PDG buffer or PSG buffer. Typically, 2×1 L of PDG or PSG buffer is used for dialysis of up to 5 mg of starting material. Examples of suitable buffers for dialysis include, without limitation, about 10 mM sodium phosphate (pH 7.4), 300 mM disaccharide, and 1.9% glycine. A preferred disaccharide is sucrose. Alternatively, the PSG buffer can contain about 40 mM, about 50 mM, about 75 mM, about 100 mM, about 125 mM, about 150 mM, about 175 mM, about 200 mM, about 225 mM, about 250 mM, about 275 mM, about 300 mM, about 325 mM, about 350 mM, about 375 mM or about 400 mM disaccharide.

Dialysis is performed for about 6-24 hours with one buffer exchange step, and the time can be varied by one of ordinary skill in the art, depending on the membrane and amount of buffer used. Typically, the initial buffer exchange is done for 3 hours to overnight (16-18 hours). In one embodiment, dialysis is performed for about 6 hours. In another embodiment, dialysis is performed for about 7, about 8, about 9, about 10, about 11, about 12, about 13, about 14, about 15, about 16, about 17, about 18, about 19, about 20, about 21, about 22, about 23 or about 24 hours. The second buffer exchange is typically performed for 16-22 hours (overnight).

After dialysis is complete, the stabilized Aβ oligomer solution is centrifuged to remove any debris. For example, centrifugation is performed for about 10 minutes at 10,000× g.

The concentration of this oligomer solution is determined by BCA assay, or another protein assay known to those of ordinary skill in the art. The sample is then lyophilized, before or after adjusting its concentration. If the concentration is adjusted, i.e., for optimal storage/lyophilization, it is adjusted by the addition of PDG or PSG buffer. Lyophilizing 80-120 μM oligomer solution typically affords optimal results. Alternatively, the sample concentration can be adjusted to about 100 μM, about 150 μM, about 200 μM, about 250 μM, or about 300 μM by the addition of PDG or PSG buffer. Typically, 200 μL aliquots of the oligomer solution are distributed into 2 mL glass vials prior to lyophilization. However, it is within the skill of one of ordinary skill in the art to adjust the volume of the oligomer sample, for optimal lyophilization.

The preceding method can be employed for various amounts of Aβ monomer starting material. The concentration of starting material useful for the above method span at least an order of magnitude. The process may be employed with, e.g., 1 mg, 2 mg, 3 mg, 4 mg, 5 mg, 6 mg, 7 mg, 8 mg, 9 mg or 10 mg Aβ monomer starting material.

Uses of the Stabilized Aβ Oligomers

For example, and without limitation, stabilized Aβ oligomer compositions are useful for the development of a diagnostic kit for the detection of AD in CSF, as well as ancillary assays used in support of the development of this kit (e.g., oligomer binding assays, MPD assay).

For example, the oligomer compositions can be subjected to the MPD assay, as described in Alzheimer's and Dementia (July 2009): 5(4) Suppl. 1 p. 193, abstract p 1-073. In this assay, fluorescently-labeled MPD peptides undergo a sequence specific conformational rearrangement in the presence of Aβ oligomers, but not Aβ fibers or monomers. The structural rearrangement changes the fluorescence profile of the MPD peptides, which can be monitored using standard instrumentation.

Stabilized Aβ oligomer compositions may also be used to study the effect of oligomers on neurons in vitro and to develop in vivo models for Alzheimer's disease by administering a composition according to the present invention to experimental subjects. For example, the stable Aβ oligomer composition can be administered to an experimental subject to determine if cognitive disruption occurs. An experimental subject whose cognition has been disrupted may serve as a model for a neurodegenerative disease, for example, Alzheimer's disease.

Oligomer Binding Assays and Development of Therapeutic Reagents

Because Aβ oligomers have been implicated in neurological dysfunction and degeneration, compounds that bind the oligomers (e.g., antibodies) are of potential therapeutic use. Stabilized Aβ oligomer composition can be used in binding assays to identify oligomer binding compounds (e.g., antibodies) that are potential therapeutic agents to treat AD.

Accordingly, stabilized Aβ oligomers can be used to screen a potential therapeutic agent by mixing the stabilized oligomer with a potential therapeutic agent to determine whether the agent binds to the oligomer, and/or whether it affects neurotoxicity of the oligomer. The neurotoxicity of Aβ oligomers can be tested both in pre-clinical behavioral testing (see Cleary et al. 2005. Nature Neuroscience 8(1): 79-84), or testing of neural tissue or cell cultures (see Barghorn et al. 2005. J. Neurochemistry 95: 834-847). Agents that bind the Aβ oligomer may be of therapeutic use, as binding may inhibit any neurotoxic activity of the oligomer. Alternatively, or additionally, fibril formation may be attenuated by administration of the therapeutic agent.

Stabilized oligomers may also be used in the development of therapeutic reagents for the treatment of AD. For example, and without limitation, biotinylated versions of SDS and F12 oligomers may be utilized in the early development of assays designed to detect the ability of reagents to inhibit oligomerization, or to disaggregate pre-formed oligomers. Detection of biotinylated Aβ42 oligomers may be accomplished, for example, using an ELISA assay in which (1) the oligomer is bound to an avidin-coated plate, and (2) detected by Avidin-HRP. Intact oligomers with at least two biotin moieties must be present for detection in this assay to occur. The ability of potential therapeutic agents to disrupt these oligomers can be tested in this assay, and reduced HRP activity correlates with disaggregation of oligomers.

Soluble Aβ oligomers may also be used for generating an antibody against an Aβ oligomer by administering an effective amount of a stabilized Aβ oligomer to a subject.

Other uses for the soluble Aβ compositions described herein include without limitations, use in a method of screening for a potential agent for the treatment of a neurological disorder. Such a method may comprise administering a stabilized Aβ oligomer composition to a first and second subject, administering a test compound to the first subject, measuring the cognitive function of the first and second subjects and comparing the cognitive function of the first and second subjects. The test compound is deemed a "hit" for further development if the cognitive functioning of the first subject is improved as compared to the cognitive function of the second subject. In a further embodiment, the neurological disorder is AD. Cognitive function can be measured by, for example, by spatial memory tasks such as the Morris Water Maze and the Radial Arm Maze, described in Byran et al. (2009). Chapter in *Methods of Behavior Analysis in Neuroscience*. Taylor and Francis Group. Other memory tasks that can be used to measure cognitive function include fear conditioning, the Y- or T-maze and object recognition, also described in Byran et al. (2009).

Alternatively, a method for screening an effective agent comprises (1) administering the stabilized Aβ oligomer to a subject, (2) measuring the cognitive function of the subject, followed by (3) administration of a test compound to the subject. Cognitive function is then measured again. The test compound is deemed effective if the cognitive functioning of the subject is improved after administration of the test compound, as compared to the cognitive function after oligomer administration.

EXAMPLES

The present invention is further illustrated by reference to the following Examples. However, it should be noted that these Examples, like the embodiments described above, are illustrative and are not to be construed as restricting the enabled scope of the invention in any way.

Methods

Sodium Dodecyl Sulfate-Polyacrylamide Gel Electrophoresis (SDS-PAGE)

SDS-PAGE was performed using standard protocols. Lyophilized Aβ oligomer samples (4 μg) were suspended in 1×LDS sample buffer and applied directly to a 12% Bis-tris gel without heat pre-treatment. Gels were run at 125 constant volts for 1 hour and proteins were visualized by coomassie-blue staining, unless otherwise indicated.

Size Exclusion Chromatography (SEC)

Sample (100 μL of ~50 μM) was added to two columns in series with UV detection at 220 nm. The SEC was performed serially on Superdex 75 10/300 GL column (GE Healthcare) and Superose 6 10/300 GL columns. These columns allow for the detection of molecules in the molecular weight range of about 4 kDa to about 1000 kDa.

Samples (~50 μM) were loaded in a volume of 100 μL to the Superdex column. Average Aβ protein MW was determined by comparing peak retention time of the sample to a standard curve of proteins of known molecular weight.

Bichinchoninic Acid (BCA) Protein Assay

Oligomer concentration was determined by the BCA assay using the BCA Protein Assay Kit by Pierce (product no. 23225 from the Thermo Scientific online catalog), with a bovine serum albumin (BSA) standard curve. Alternatively, oligomer concentration can be determined using the p660 Protein Assay Kit by Pierce (product no. 22662 from the Thermo Scientific online catalog). The mg/mL concentrations determined by either the BCA or p660 assay are converted to molar concentrations using the monomeric molecular weight of the oligomer species prepared (e.g. 4514 g/mol for Aβ42 preparations).

Thioflavin T (ThT) Fluorescence Assay Analysis

ThT is an azo-free dye that fluoresces when it binds to the crossed-β-pleated sheet structure common to Aβ fibrils (Ventura and Serrano (2003). *Spectroscopy*, 17, pp. 647-652. Accordingly, an increase in fluorescence in this assay is directly correlated with Aβ fibril formation and presence.

ThT reaction consisted of 7.5 μM ThT (Sigma) and 2.5 μM stabilized Aβ42 oligomer in 1×PBS in a final volume of 200 μL. Reactions were incubated for 10 minutes at room temperature to determine if ThT bound to the oligomer samples. Samples were then read on a Tecan fluorescence instrument (Männedorf, Switzerland, excitation at 445 nm, fluorescence emission at 460-540 nm; bandwidth=5 nm). Fluorescence emission was then compared to the fluorescence generated by both Aβ42 fibril-ThT reaction, and Aβ42 monomer-ThT reaction. The Aβ42 fibril-ThT reaction served as a positive control, and ThT reactivity for each oligomer is expressed as percent Aβ42fibril reactivity.

Reverse Phase Liquid Chromatography (RPLC)

Oligomer samples obtained and stored as described in the examples, were diluted 1:1 in mobile phase A (water/0.1% formic acid v/v). 50 μL of the mixture was then injected into a Waters Symmetry300 C4 column (4.6×150 mm, Pore size: 5 μm, Part No. 186000288) with Symmetry 300 C4 guard column. Chromatography was performed using a 1% B/min gradient with the second mobile phase consisting of Acetonitrile (ACN)/0.1% formic acid. Oligomers were detected by spectroscopy, using 215 nm absorbance. This method can distinguish chemical modifications to Aβ oligomers such as deamidation and oxidation.

Misfolded Protein Diagnostic (MPD) Assay

The MPD assay quantitates Aβ oligomer by its dose-dependent interaction with a pyrenated peptide, for example, pyrenated ALZ peptide 22 or pyrenated Pronucleon™ peptide. Upon binding to Aβ oligomer, pyrenated peptides have altered fluorescence properties that can be measured in a 96-well format using a standard fluorometer. A variant of the assay has been used previously to detect the misfolded prion protein (Pan et al. (2007) *Transfusion* 47 1418-1425).

Binding of an Aβ oligomer to either Pronucleon™ or ALZ peptide causes a conformational change in the peptide, which in turn, causes pyrene to exhibit altered fluorescence properties. The conformational change is not observed when either peptide is incubated with Aβ monomer or fibril (see FIG. 9). Therefore, by measuring fluorescence of pyrene, the MPD assay quantifies the amount of Aβ oligomer in a sample. In some instances, the MPD assay measures binding of pyrenated peptide to both Aβ oligomer and Aβ fiber (i.e., the assay is not specific for Aβ oligomer).

The MPD assay was performed as follows, unless otherwise indicated. Reactions were performed in a 96-well plate format. Pyrenated ALZ peptide 22 (200 μM in hexafluoroisopropanol (HFIP), which consists of Aβ residues 16-35 with two point mutations (custom-made by Scilight, Inc. Beijing, China) was initially diluted to 87.5 nM in 12.5 mM HEPES, pH 7.0.

SDS and/or F12 Aβ oligomer compositions—typically 100 μM in PSG buffer, prepared as described below in Examples 1 and 2, respectively—were diluted to stock concentrations of 1.5 μM, 0.5 μM, 0.167 μM and 0 μM (no template control) in water.

40 μL of each oligomer preparation was combined with 160 μL ALZ peptide 22 (or other pyrenated peptide variant) directly in the wells of a 96-well plate. The final conditions for each 200 μL reaction were as follows 10 mM HEPES (pH 7.0), 70 nM ALZ peptide 22, and 0.3 μM, 0.1 μM, 0.033 μM, or 0 μM Aβ42 oligomer composition.

Plates were incubated at 37° C. (unless specified otherwise) in the dark, and fluorescence readings were taken using a TECAN fluorometer at Time 0, 3 hrs, and overnight (18-22 hours). The excitation wavelength was 350 nm, and emission scan was 365-600 nm.

The areas of the self-fluorescence emission peaks from 370-410 nm were then calculated, and compared to control values to determine the response.

The response has been shown to be dose and time dependent the samples incubated overnight with the fluorescently labeled peptide are expected to give a higher fluorescence than the 0 and 3 hour time points. Similarly, the higher the concentration of Aβ oligomer composition, the greater the fluorescence response.

Example 1

Production of SDS Amyloid-β Oligomers

This example sets forth a procedure for producing PSG-stabilized SDS Aβ oligomers.

1.0 mg of commercially obtained Aβ1-42 (dried in HFIP-coated film, Anaspec, Product No.) was dissolved in 44 µL dimethyl sulfoxide (DMSO, Acros, Product No. 61097.) The mixture was sonicated for 30 seconds at 25 Watts (W), and briefly vortexed. 2 mL of phosphate-buffered saline (1×PBS, pH 7.4) was then added to the mixture, followed by addition of 131 µL of 2% SDS solution.

The resulting mixture (4.3 mM SDS, 100 µM Aβ1-42, 0.9×PBS) was incubated at 37° C. for 24 hours. The mixture was then vortexed briefly, aliquoted into two 1.5 mL microcentrifuge tubes, and centrifuged at 3000×g for 20 minutes to pellet and remove any Aβ fibrils. The resulting supernatant was transferred to a 4 mL Millipore ultrafiltration device (30 kDa molecular weight cut off), and concentrated approximately 5-fold (from ~2 mL to ~0.4 mL) by centrifugation at 1500×g for 5-10 minutes.

Concentrated sample was dialyzed against 1 liter of one of the following buffers: (1) PSG buffer containing 10 mM sodium phosphate (pH 7.4), 300 mM sucrose, and 1.9% glycine. Similar results were obtained when dialysis was performed against PSG40 formulation buffer containing 10 mM sodium phosphate (pH 7.4), 40 mM sucrose, and 1.9% glycine; and PSG buffer/300 mM Sucrose, 0.01% Tween20. Dialysis against 0.25×PBS was performed as a negative control.

Dialysis was continued for 6-24 hours, with one buffer replacement step after 3-hours. Sample was then transferred to a 1.5 mL microcentrifuge tube and centrifuged at 10,000×g for 10 minutes to remove Aβ fibrils and supernatant transferred into a new microcentrifuge tube. Protein concentration of the supernatant was determined by BCA assay, and adjusted to 110 µM by dilution with the appropriate formulation buffer. The solution was distributed in 200 µL aliquots into 2 mL glass vials, and lyophilized. This method has been successfully scaled-up 5-fold (5.0 mg of starting material), and can be scaled up by at least 10-fold or higher without modification.

Example 2

Production of Amyloid-β Oligomer Composition with F12

F12-stabilized Aβ oligomers were prepared as follows:
1.0 mg of commercially obtained Aβ1-42 (dried in HFIP-coated film) was dissolved in 44 µL, DMSO. This mixture was sonicated for 30 seconds at 25 W, and then briefly vortexed. 2.2 mL of the cell culture medium DMEM/F12 (1:1) (no phenol red) (Mediatech/Cellgro) was added, vortexed for 30 seconds. The mixture was then incubated at 37° C. for 18-24 hours.

The resulting solution was vortexed briefly, separated into two aliquots, and each was transferred into a separate 1.5 mL microcentrifuge tube and centrifuged at 14,000×g for 10 minutes at 4° C. to remove any Aβ fibrils. The supernatant was transferred into a 4 mL Millipore ultrafiltration device (30 kDa MWCO). The Aβ oligomer solution was concentrated approximately 5-fold (from ~2 mL to ~0.4 mL) by centrifugation at 1500×g for 5-10 minutes.

The sample was then dialyzed into 1 L of PSG formulation buffer (300 mM sucrose). Dialysis continued for 6-24 hours, with one buffer replacement step at 3-6 hours. After dialysis was complete, the sample was transferred into a 1.5 mL centrifuge tube and vortexed at 10,000×g for 10 minutes. The supernatant was then transferred into a sterile tube. The concentration of the final solution was determined by BCA assay, and subsequently adjusted to 110 µM by dilution in PSG formulation buffer. Finally, 200 µL aliquots of the F12 oligomer solution were distributed into 2 mL glass vials, and lyophilized.

This method has been successfully scaled 5-fold (5.0 mg of monomer starting material), and can be conceivably scaled up to 10-fold or higher without modification.

Example 3

Preparation of Biotinylated Oligomers

SDS and F12 Aβ42 oligomers were prepared as described above for Examples 1 and 2, with the following modification. Biotinylated Aβ 1-42 monomer resuspended in DMSO was mixed with unlabelled Aβ42 monomeric starting material (in DMSO) in a 1:10 mol:mol ratio. The monomer solutions (SDS or F12 oligomers containing biotinylated Aβ42 monomers) were then processed as described above in Examples 1 and 2.

Figure 10:
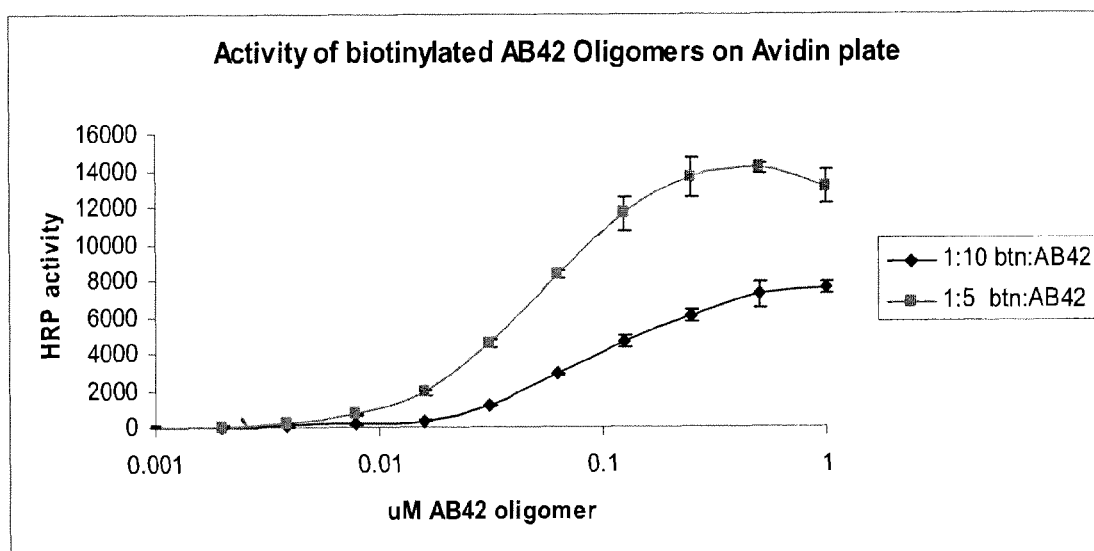
FIG. 10 shows the detection of biotinylated Aβ42 oligomers in an ELISA assay in which (1) the oligomer is bound to an avidin-coated plate, and detected by avidin-HRP.

FIG. 10 shows the detection of biotinylated Aβ42 oligomers in an ELISA assay. The oligomer preparation was bound to an avidin-coated plate, and detected by avidin-HRP. In this assay, intact oligomers with at least two biotin moieties must be present for detection to occur. This assay can test the ability of potential therapeutic agents to disrupt oligomer formation. For example, an agent that disrupts oligomer formation (or disaggregation of oligomers) would also disrupt the binding of the oligomer composition to avidin. In this assay, reduced HRP activity correlates with disaggregation of oligomers and/or disruption of oligomer formation.

Example 4

Evaluation of Pronucleon™ Peptide Binding to Aβ Oligomers

The folded states of the components of the Aβ oligomer compositions were evaluated using a Pronucleon™ binding assay. This example evaluated the binding of biotinylated F12 Aβ oligomers to two Pronucleon™ peptide variants, a "wildtype" sequence, which consisted of Aβ sequence 16-35; and p22, in which two point mutations were introduced in order to (1) induce an α-helical structure that was expected to reduce background excimer fluorescence, and (2) enhance solubility.

Pronucleon™ peptides were previously designed to mimic the mechanism of misfolded prion proteins (Pan et al. (2007). *Transfusion* 47 1418-1425). Each Pronucleon™ peptide was labeled with pyrene butyric acid at the N- and C-termini. Under aqueous conditions, Pronucleon™ peptides exhibit excimer fluorescence (emission maxima at ~445 nm and ~485 nm) in the absence of substrate, but switch to a primarily self-fluorescent signal (emission maxima at ~380 nm and ~400 nm upon binding Aβ oligomers. p22 Pronucleon™ peptide's fluorescence profile was not altered in the presence of either Aβ40/42 monomers or Aβ40/42 fibrils (see FIG. 9).

Reagents

200 µM Pronucleon peptide stocks (prepared by Scilight Inc., Beijing, China) were prepared in 100% HFIP, and stored at −80° C. until use. Before incubation with Aβ oligomers, 25 μL Steptavidin-derivatized Dynabeads® (MyOne™ Streptavidin T1, Invitrogen) were washed twice with PBS, and blocked for 2 hours with SuperBlock (Pierce, Part Number 37515). Next, the Dynabeads® were equilibrated with 1× working buffer (10 mM HEPES, 0.05% Tween 20). After 30 min. of incubation with the working buffer, the beads were sequestered at the bottom of the reaction vessel with a magnet. The beads were then subjected to three wash steps, each with 1 mL of working buffer. The beads were then resuspended to 25 μL in 1× working buffer, for use in the Aβ oligomer binding assay.

General Experimental Description

F12 biotinylated oligomers were manufactured according to the procedure outlined in Example 3. The biotinylated oligomer solution was reacted with a Pronucleon™ peptide, followed by capture of the complex on avidin resin. The biotin-avidin binding reaction was performed in 1× working buffer.

Detailed Experimental Description

50 μL of 0.1 μM biotinylated F12 oligomers (prepared as described above) were co-incubated for 2 hours at room temperature with 50 μL of a Pronucleon™ peptide. The Pronucleon™ peptide had a concentration ranging from 0 μM (negative control) to 4 μM. After the reaction reached equilibrium (i.e., 2 hours), the biotinylated F12 oligomer compositions were subjected to a streptavidin binding reaction, by co-incubating the biotinylated Aβ oligomers with 25 μL Dynabeads® for 2 hrs at room temperature.

The beads and their associated proteins were extracted by boiling with 25 μL of 1×LDS buffer for 5-10 min. The beads and their associated proteins/peptides were then analyzed by SDS-PAGE (10 μL of each sample). The gel was silver stained to ensure maximal detection of amyloid proteins. The results from this experiment are presented in FIG. 1.

The results show that biotinylated F12 Aβ 42 oligomers from Example 3 can bind to both wild type Pronucleon™ peptide and a variant Pronucleon™ peptide, p22. Addition of F12 biotinylated oligomers induced formation of oligomer-peptide complexes that were precipitated by streptavidin bearing beads. The F12 oligomer bound to almost 100% of the Pronucleon™ peptide (comparison of the samples in lanes 18 and 19). This demonstrates that a high ratio of peptide was present in the peptide-oligomer complexes.

Example 5

Characterization of SDS Aβ Oligomers and 14 Day Stability Studies

Figure 2:
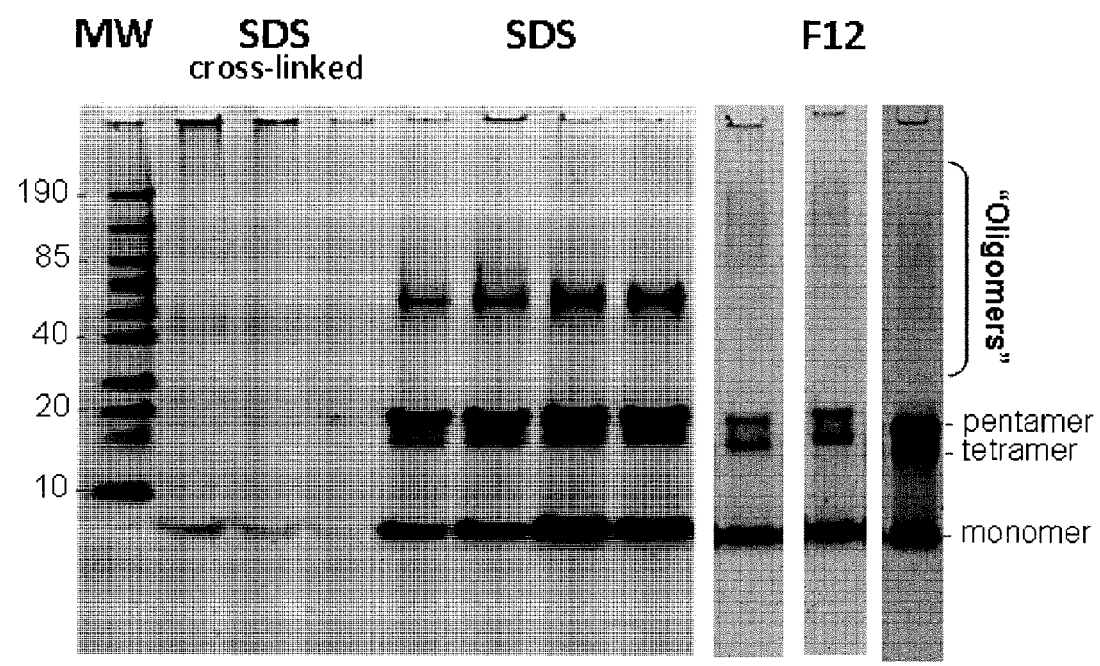
FIG. 2 is an image of a coomassie-blue SDS-PAGE gel loaded with different lots of stabilized SDS Aβ42 oligomer samples.

The purity and the stability of the Aβ oligomer compositions prepared by the procedure outlined in Example 1 were determined using stability and functional assays, as follows:
SDS-PAGE Lyophilized SDS oligomer samples were suspended in 1×LDS sample buffer (Invitrogen, Part Number NP0008), and 10 μL of each sample was applied directly to a 12% Bis-tris gel without heat pre-treatment. Gels were run and visualized as described above. Silver stained SDS-PAGE gels are shown in FIG. 2 and the percentages of monomer and oligomer quantified from gels are presented in Table 2. Although monomers, pentamers and tetramers were also present, FIG. 2 shows that a substantial portion of the SDS oligomers were present in a distinct form, as seen by a broad band in the range of 40-80 kDa (as compared to protein standards). For purposes of analysis, all bands above monomer are considered to Aβ oligomer. These results show that the Aβ oligomer species in the SDS oligomer composition are stable, as distinct oligomer bands were present, and no high molecular weight species bands (i.e. bands present at the top of the gel, near the wells) were present.

The percent oligomer in each sample was then calculated by measuring the optical density of each band. As can be seen in Table 2, the percent oligomer ranged from 60-71%.

Figure 4:
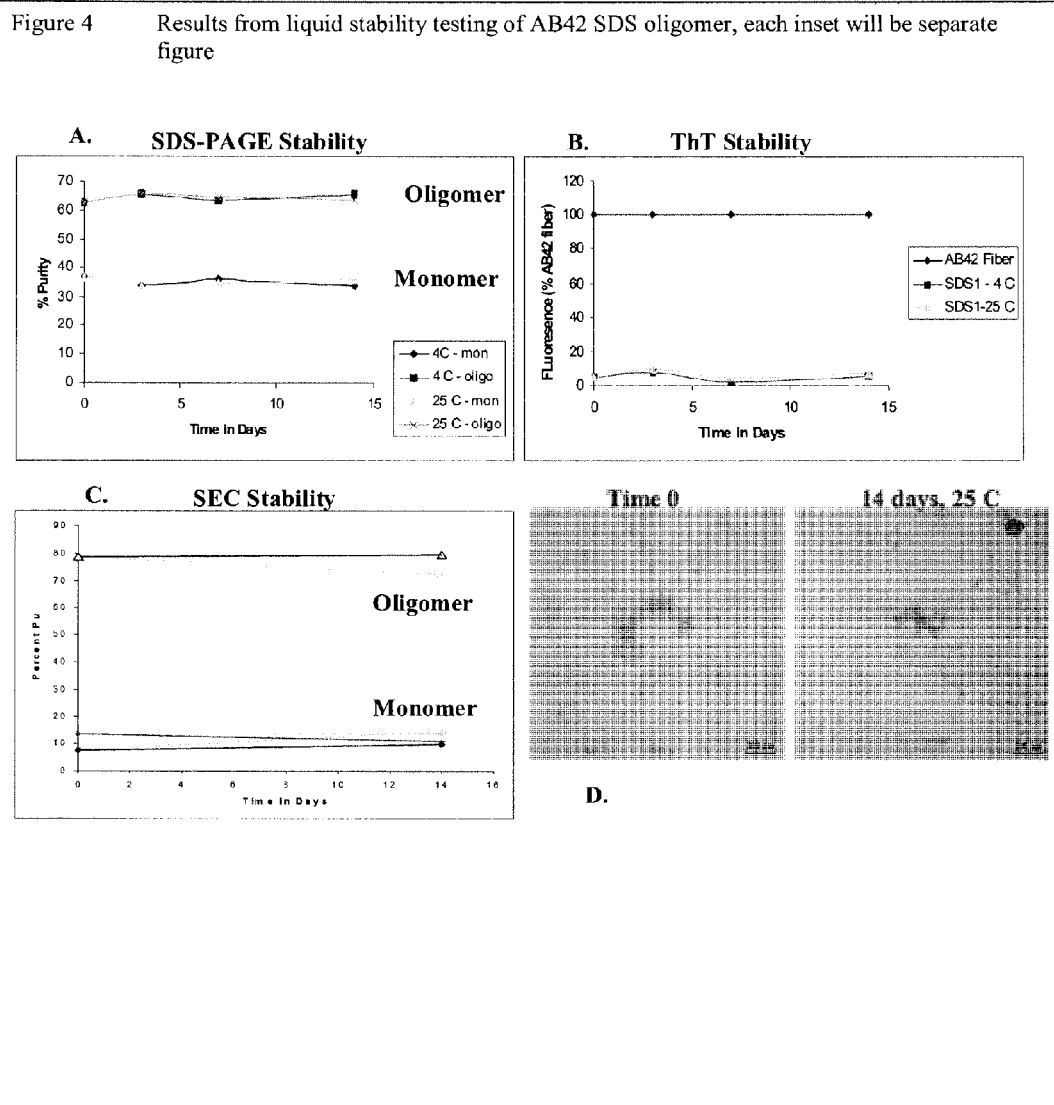
FIG. 4 shows graphs illustrating the stability profile of two sucrose-stabilized SDS Aβ42 oligomer preparations as a function of time. Panel A shows changes in the oligomer and monomer content of preparations stored at 4° C. and 25° C. over 14 days as determined by SDS-PAGE; Panel B shows changes in the oligomer and monomer content of the 4° C. and 25° C. samples over 14 days as determined by SEC; Panel C shows the ThT staining of the two SDS oligomer preparation over 14 days compared to an Aβ42 fibril control sample; and Panel D shows an electron micrograph of an SDS-stabilized Aβ42 oligomer at Time 0 and after 14 days incubation at 25° C.

SDS oligomer compositions were subjected to short-term stability tests and analyzed by SDS-PAGE. Lyophilized SDS oligomer compositions were resuspended in water, and incubated at 4° C. and 25° C. in the dark. The preparations were analyzed by SDS-PAGE after incubation for various time periods (0 days, 3 days, 7 days and 14 days) (FIG. 4A). The oligomer compositions remained stable over a 2 week period, as the optical density of the oligomer species band for each time point tested, at both 4° C. and 25° C. storage, was substantially the same (FIG. 4A). As such, storage temperature of 4° C. and 25° C. did not affect the stability of the oligomer compositions, as determined by SDS-PAGE.
Size Exclusion Chromatography Samples prepared according to the process of Example 1 were subjected to size exclusion chromatography (SEC). Soluble Aβ species of different sizes (e.g., Aβ monomers, Aβ oligomers) elute at different rates, and accordingly, the chromatography process gives an indication of the average MW of Aβ oligomers present in the sample, as well the proportion of Aβ oligomers and monomers.

Figure 3:
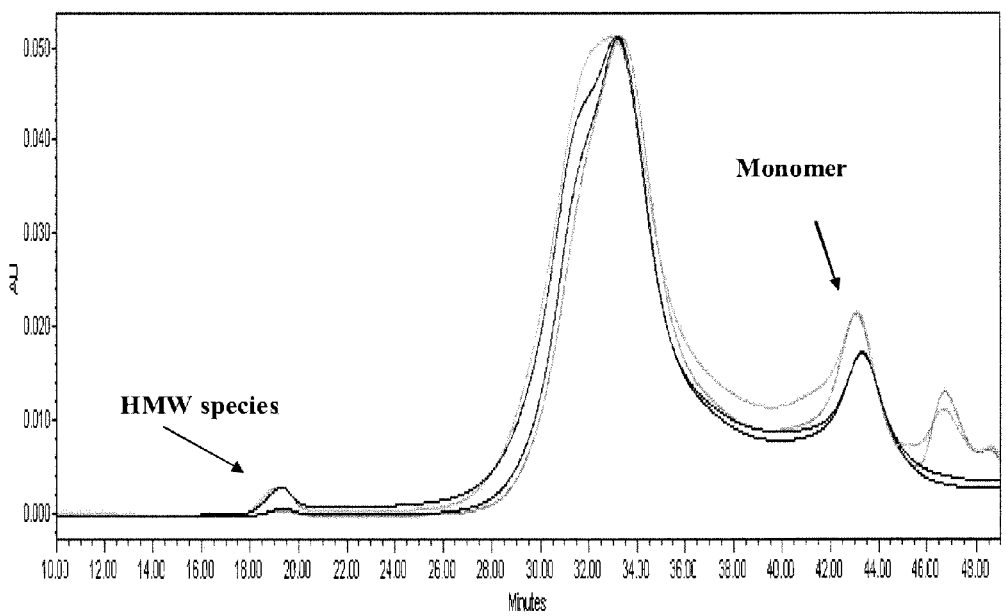
FIG. 3 is a size exclusion chromatography (SEC) profile of the stabilized SDS Aβ42 oligomer lots prepared in Example 1.

The native oligomeric state of the SDS oligomers, as determined by SEC, demonstrated that the oligomer composition was moderately reproducible, in terms of percent oligomer in each composition (74.8-90.7% oligomer in each lot made, see Table 2). The chromatographic profile for each Aβ oligomer composition was characterized by (i) very low amounts of high molecular weight (HMW) species, defined as the variants that elute with the excluded volume; and (ii) a relatively low proportion of monomer (9.2-17.9%) (see FIG. 3 for the SEC profiles of various oligomeric compositions prepared according to Example 1). The oligomeric portion of the oligomeric composition is estimated to have a molecular weight ranging from 60-140 kDa.

SEC was also performed on Aβ oligomer compositions at various points (0 days, 3 days, 7 days, 14 days) to determine whether the oligomer concentration in each composition remained substantially the same (FIG. 4B). Time 0 corresponded to the time immediately after the lyophilized composition was resuspended in water. An increase in HMW species is an indication that the oligomer composition is unstable over time. As can be seen in FIG. 4B, the percent of oligomer species in the in the oligomer composition remained substantially the same over a 2 week period, at ~80% Aβ oligomer per composition. The composition stored at 25° C. had approximately 12% monomer, and the composition stored at 4° C. had approximately 10% monomer. The percentage of monomer and oligomer in the composition, as shown in FIG. 4C, remained substantially the same over the 14 day period.
ThT 14 Day Stability Measurements In order to functionally characterize the long term stability of the Aβ oligomers in the compositions, lyophilized Aβ oligomer compositions were prepared by the process of Example 1, resuspended in water, and stored at either 4° C. or 25° C., in the dark. At various time points (0 days, 3 days, 7 days, 14 days), the compositions were subjected to a ThT reaction, as described above. An increase in fluorescence in this assay is directly correlated with the presence of Aβ fibrils, and Aβ oligomer instability.

ThT reactivities of the oligomer compositions were uniformly low over all time periods tested (0 days, 3 days, 7 days, 14 days; 3%-11%, as compared to Aβ42 fibrils, FIG. 4C). These results show that the oligomer portion of the composition is a distinct species from Aβ42 fibril. Additionally, the ThT response of oligomers was comparable to that of Aβ42 monomer control (data not shown). Further, for each time point and temperature tested, the concentration of oligomer was substantially the same, indicating that Aβ fibrils did not form from the oligomer species.

Electron Microscopy

Aβ oligomer samples prepared as described in Example 1 were also visualized by electron microscopy (FIG. 4D). Samples (resuspended in water) were vortexed gently and pulled in and out of a micropipette 3-4 times. Next, a 5 μL aliquot of sample was allowed to settle on a collodion and carbon coated copper grid. After 90 seconds, excess sample was removed and the grid was washed with two drops of 100 mM ammonium acetate, and then stained with uranyl formate for 90 seconds. All images were recorded at a negative magnification of 50,000×.

Another aliquot of the sample was stored in the dark for 14 days, at 25° C. A comparison of electron micrographs of Time 0 and 14 days showed that the samples were remarkably similar, and that there was no indication of fibril formation (FIG. 4D).

TABLE 2

Aβ SDS oligomer characterization

| Test | Method | | Aβ42 SDS oligomers | | | | |
|---|---|---|---|---|---|---|---|
| | | | Lot 1 | Lot 2 | Lot 3 | Lot 4 | Lot 5 |
| Appearance | Visual Inspection | | CCP* | CCP | CCP | CCP | CCP |
| Purity | SEC | % Monomer | 16.3% | 11.1% | 13.6% | 9.2% | 17.9% |
| | | % Oligomer | 74.8% | 81.4% | 78.5% | 90.7% | 81.5% |
| | | % HMW | 0.3% | 1.2% | 0.2% | 0.1% | 0.1% |
| Purity | RP-HPLC | % Main Peak | 77.7% | 79.0% | 69.6% | 66.9% | 78.5% |
| Purity | SDS-PAGE | % Monomer | 37% | 29% | 37% | 40% | 32% |
| | | % Oligomer | 63% | 71% | 63% | 60% | 68% |
| ThT reactivity | Fluorescence | % Aβ42 Fibril Control | 10% | 3% | 8% | 11% | 8% |

*Clear, colorless, essentially free from particulate matter

Summary

Oligomer compositions were analyzed by various functional and analytical assays to determine if the Aβ oligomers formed higher order fibrils after the initial preparation (as given in Examples 1-3), and after 14 days. The presence of high molecular weight species over time indicated that Aβ fibrils had already formed or were in the process of forming. Oligomer compositions prepared with PSG buffer as in Example 1 were stable over a period of 14 days. These preparations can thus be used in the preparation of screening and diagnostic assays, which often take weeks or even months to optimize, in that they demonstrate substantially the same physical properties over time.

Additionally, these results show that a PSG-stabilized Aβ oligomer composition prepared by the method of Example 1, can be used over a 2 week period in the development of screening assays, without the formation of Aβ fibrils from the oligomers in the composition. Additionally, because aliquots of an oligomer composition can be used in experiments conducted at different times, the results are more reproducible and more trustworthy with the oligomer compositions provided herein, as compared to commercially available reagents.

Example 6

Thirty Three Day Stability Study of Aβ SDS Oligomers

Lyophilized Aβ42 oligomer samples prepared by the method outlined in Example 1 were each resuspended in 200 μL water, and incubated at either 4° C. or 25° C., in the dark. The samples were characterized at four time points—(1) 0 days, (2) 7 days, (3) 14 days and (4) 30 days. Time 0 corresponded to the time immediately after the lyophilized sample was resuspended in water.

No visible particulate matter was observed at any of the time points tested.

Aliquots were subjected to SDS-PAGE at the four time points, to determine the MW of the various species in the Aβ oligomer samples. The sizing data (Table 3) showed that the oligomer species was stable for 2 weeks at 4° C. However, the percentage of oligomer species observed in the composition, as measured by SDS-PAGE, increased from 33% to 47% over the course of the study when the oligomers were incubated at 25° C., indicating some changes in conformation of the oligomers (Table 3). Resuspended lyophilized oligomer compositions were substantially stable at both 4° C. and 25° C. Greater stability, however, was observed for resuspended oligomers at 4° C.

Figure 5:
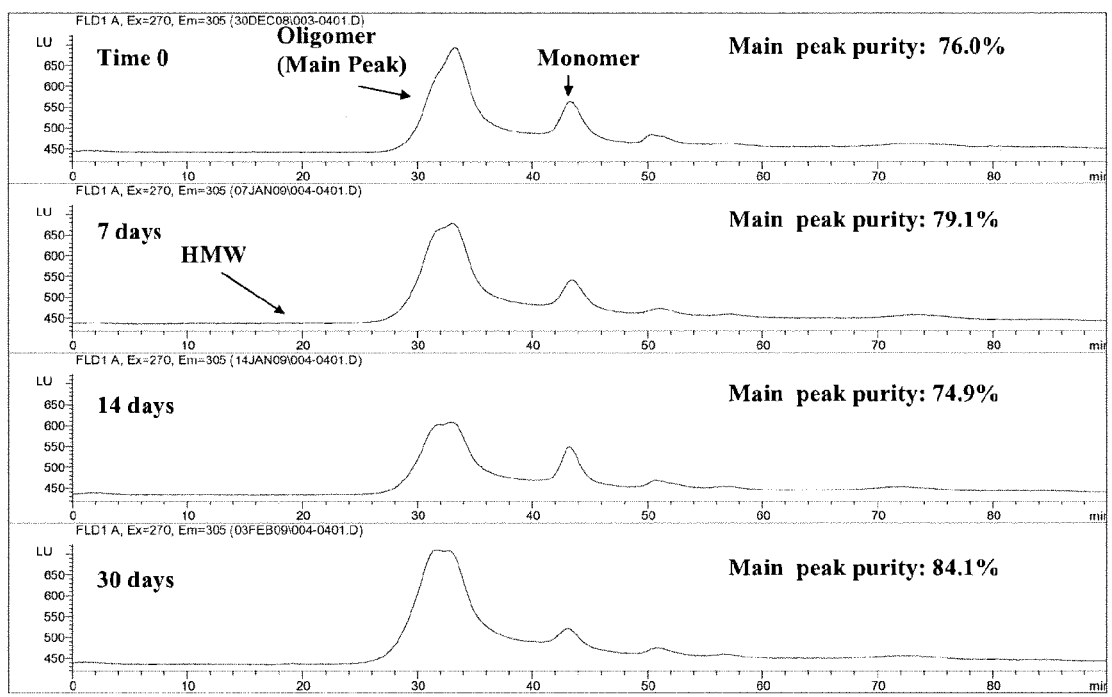
FIG. 5 shows SEC profiles of a sucrose stabilized SDS Aβ42 oligomer at various time points after preparation (0 days, 7 days, 14 days, 33 days) when incubated as a liquid at 4° C.

To assess the stability of the Aβ oligomer preparations, the Aβ oligomer sample (stored at 4° C.), was subjected to SEC, at 0 days, 7 days, 14 days and 30 days (FIG. 5). In general, if an Aβ oligomer composition is stable, it should exhibit almost substantially the same SEC profile over time, for each time point tested.

FIG. 5 and Table 3 show the results of this experiment. The overall size profile appeared mostly unchanged over time, although there was a slight increase in the proportion of oligomeric species and corresponding slight decrease in the proportion of monomer from Time 0 to 30 days. There was no indication of formation of high molecular weight (HMW) species. Consistent with the SDS-PAGE data, SEC profiles of samples stored at 25° C. showed an increase in percentage of oligomer over time. However, no HMW species were observed for these preparations (Table 3).

Formation of Aβ fibrils was also measured in a ThT assay. Aβ oligomer compositions were subjected to the ThT assay at each of the four time points given above. For each sample, at each time point and temperature tested, the percent fluorescence stayed relatively constant (Table 3). These results suggest that the oligomer preparations were stable over the time points tested and did not form higher order fibrils. These data, together with SEC and SDS-PAGE results, demonstrate that the Aβ oligomers prepared as described herein can be used over at least a 30 day period, without the formation of Aβ fibrils.

Lastly, the Aβ oligomer samples (4° C. and 25° C. storage) were subjected to the MPD assay at time 0, 14 days and 30 days. This particular version of the assay measures oligomer and fiber presence in a sample by a binding reaction with a pyrenated Pronucleon™ wild type peptide. In this version of the assay, when an Aβ oligomer or fiber binds the peptide, the fluorescence profile of pyrene (present in the peptide) is altered. In the absence of binding, no change in pyrene fluorescence is observed. When each stability sample was subjected to the MPD assay, no significant changes in oligomer/fiber binding to the Pronucleon™ peptide was observed over time, as measured by pyrene fluorescence (Table 3). The results from the MPD assay indicate that the Aβ oligomers remained stable in the disaccharide stabilized oligomer composition, for an extended period of time (30 days), when stored either at 4° C. or 25° C.

Taken together, the data presented in Example 5 indicated that the Aβ42 SDS oligomer compositions were stable and exhibited consistent structural properties over at least a thirty three day period, as the components in each composition were substantially the same over time, and the compositions delivered a consistent response when subjected to both the MPD and ThT assays, especially the samples stored at 4° C.

glycine), (2) PSG 40 buffer (10 mM sodium phosphate, 40 mM sucrose, 1.9% glycine) and (3) 0.25×PBS.

Each oligomer composition was prepared according to the method in Example 1, with the only difference being the dialysis buffer, as given above. Lyophilized samples were resuspended in 200 μL water and incubated at 25° C. for 0 days, 14 days and 30 days.

0.25×PBS was used in the study because it is the solvent in which amyloid oligomers are typically stored/dialyzed in after their production (e.g., Barghorn et al., 2005, J. Neurochemistry, 95:834-847). Both compositions prepared using a PSG buffer exhibited a higher percentage of oligomer at the first time point tested, as compared to the PBS preparation (time 0), indicating that oligomer formation is favored in PSG buffer, as compared to PBS. No visible particulate matter was detected throughout the study for any of the samples.

SDS-PAGE

Table 4 also gives the results of an SDS-PAGE time course experiment on the samples (0 days, 14 days, 30 days). At each time point, components of each oligomer composition were separated by SDS-PAGE, as described in the beginning of the Example section. The optical density of each band was then measured, to give the percentage of each distinct species present in the sample. Each of the compositions showed an increase in oligomer formation over time.

Size Exclusion Chromatography

The different Aβ oligomer preparations were also subjected to SEC.

TABLE 3

Stability table of Aβ42 SDS oligomers in PSG buffer: 33-day accelerated liquid stability

| | | 4° C. | | | | 25° C. | | | |
|---|---|---|---|---|---|---|---|---|---|
| | | Time 0 | 7 days | 14 days | 33 days | Time 0 | 7 days | 14 days | 33 days |
| Visual Inspection | | CCP* | CCP | CCP | CCP | CCP | CCP | CCP | CCP |
| SDS-PAGE | % Oligomer | 33% | 34% | 33% | 34% | 33% | 41% | 42% | 47% |
| | % 16/20 kDa | 42% | 41% | 45% | 43% | 42% | 36% | 39% | 33% |
| | % Monomer | 25% | 25% | 21% | 23% | 25% | 22% | 19% | 20% |
| SEC | % HMW | 0% | 0% | 0% | 0% | 0% | 0% | 0% | 0.1% |
| | % Oligomer | 76.0% | 79.1% | 74.9% | 84.1% | 76.0% | 88.3% | 85.7% | 88.8% |
| | % Monomer | 24.0% | 20.9% | 25.1% | 15.9% | 24.0% | 11.7% | 14.4% | 11.1% |
| MPD assay** | Ln Excimer Gain | 0.5 | | 0.6 | 0.6 | 0.5 | | 0.6 | 0.6 |
| Fluorescence | % Aβ42 Fibril Control | 12% | 14% | 12% | 9% | 12% | 13% | 15% | 12% |

*CCP = Clear, colorless, essentially free of particulate matter
**Functional assay showing reactivity of oligomer with Pronucleon™ peptide Example 7

Comparison of Aβ Stabilities in Different Dialysis Buffers

Example 6 provided evidence that the oligomers dialyzed into PSG buffer were stable in a liquid formulation over a period of at least 33 days. To determine whether the PSG buffer gave greater oligomer stability than a buffer commonly used in Aβ oligomer composition preparation, the following study was conducted.

A 30-day Aβ42 SDS oligomer stability study was conducted to compare the stability of oligomer compositions prepared with three different dialysis buffers—(1) PSG 300 buffer (10 mM sodium phosphate, 300 mM sucrose, 1.9%

Figure 6:
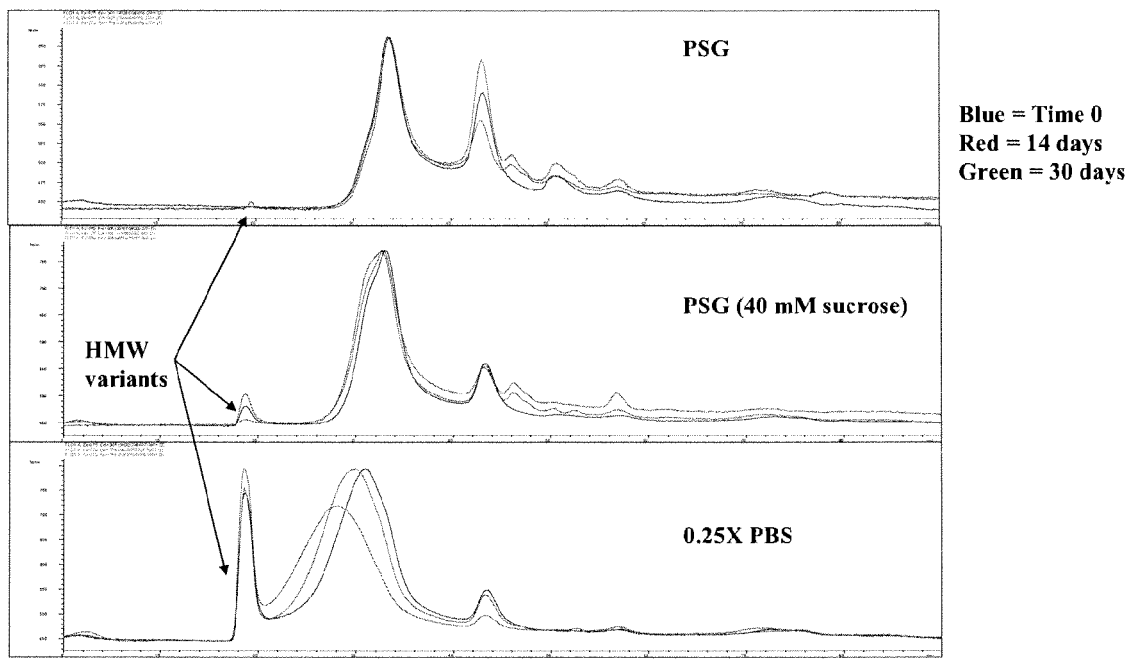
FIG. 6 shows SEC profiles of SDS Aβ42 oligomer samples prepared with different dialysis buffers, and stored as a liquid at 4° C. for 30 days).

Each of the three samples was subjected to SEC at various time points over a 30 day period (0 days, 14 days, 30 days). As shown in FIG. 6, the oligomer composition prepared in PSG buffer with 300 mM sucrose exhibited a consistent profile over the time periods tested—each oligomer peak overlaps and is the same height. In contrast, the oligomer peaks for the 0.25×PBS peaks are not consistent, indicating that different species of oligomers are forming at various times during the 30 day experiment, in the PBS dialyzed composition. SDS-PAGE did not have the resolution to show this difference. Additionally, oligomers dialyzed against 0.25×PBS contained a large proportion (15-18%) of HMW species, over an order of magnitude higher than what was observed for the two compositions prepared in PSG dialysis buffer (300 mM and 40 mM sucrose). These data demonstrate that Aβ oligomer compositions prepared in PBS do not maintain a stable profile, and are likely to readily form fibrils. The data also show that oligomers prepared with 300 mM sucrose PSG buffer are slightly more stable than Aβ oligomers prepared in PSG buffer with 40 mM sucrose, since the proportion of HMW species is lower at all time points in the formulation with 300 mM sucrose.

ThT and MPD Assays

The Aβ oligomer compositions were also functionally characterized by subjecting them to both the ThT and MPD assays, as described above. Oligomer compositions dialyzed against 0.25×PBS showed an elevated ThT response at all time points compared to the other samples, indicating that some fibrillization has occurred under these conditions (see Table 4). In contrast, the ThT response of SDS oligomers in the two PSG buffer variants was comparable to Aβ42 monomer (data not shown).

Figure 7:
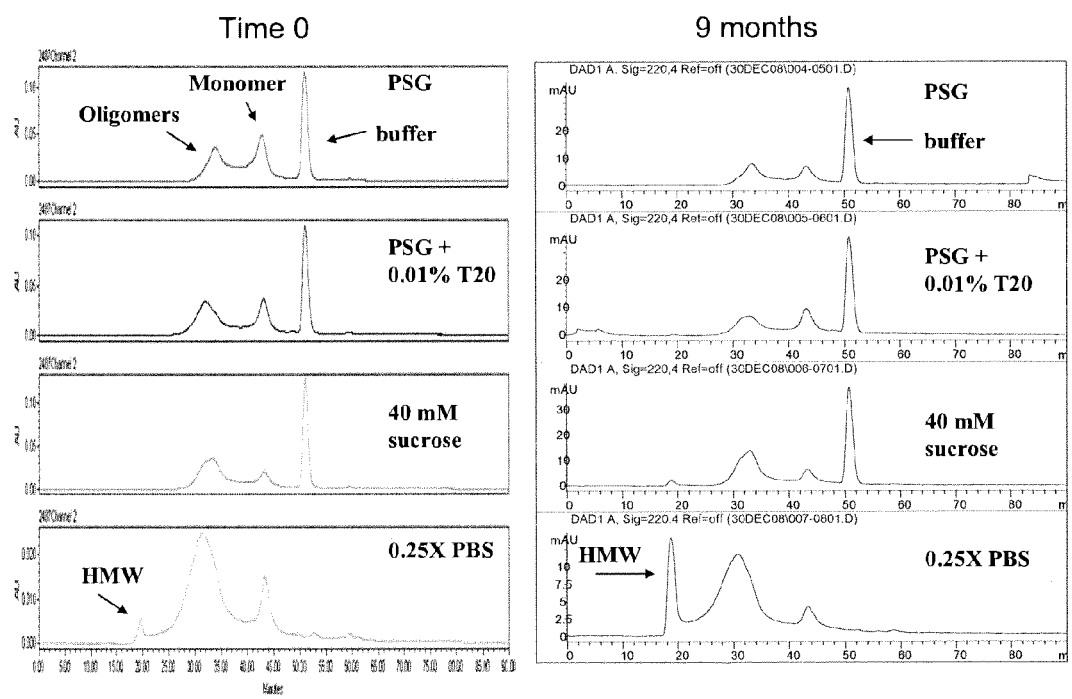
FIG. 7 shows SEC profiles of Aβ42 SDS oligomers in the presence of four alternative formulation buffers immediately after preparation, and at 9 months incubation at 4° C. in the lyophilized state.

There was no difference in performance of the three preparations in the MPD functional assay. The MPD assay used in this experiment was a version in which both fibrils and oligomers were reactive with the pyrenated peptide. The results from the MPD assay under these conditions, taken together with the results from the ThT assay, suggest that oligomers under all three conditions have not been dissociated to monomers during the stability study.

present in each composition, and whether these species, and their respective percentages in the compositions, were comparable over the nine month period. The results from this study are given in FIG. 7 and Table 5. Whereas the size profiles of the SDS oligomers in each of the PSG formulation buffers (samples (1)-(3) as described above) stayed substantially the same over time (each species eluted at the same time at each time point, and relative proportions of monomer, oligomer and HMW species was similar), oligomer compositions dialyzed against 0.25×PBS were not stable, as HMW variants increased substantially from 3.3% to 18.2% in the lyophilized state (see FIG. 7 and Table 5). These data show that PSG buffer is a superior stabilizing solvent compared to the solvent typically used to store Aβ oligomer preparations.

The compositions prepared with PSG buffer containing 40 mM sucrose contained approximately 75% oligomer species at both time points tested, which was the highest percentage of oligomers, compared to the other compositions. However, the percentage of monomer decreased from 26.3% to 20.6%, and the HMW species increased from 0.2% to 3.8%. These data suggest that fibril formation is taking place over time.

TABLE 4

Stability table of Aβ42 SDS oligomers in two PSG buffer variants and 0.25C PBS: 30-day accelerated liquid study

| | | | PSG (300 mM sucrose) | | | PSG (40 mM sucrose) | | | 0.25X PBS | | |
|---|---|---|---|---|---|---|---|---|---|---|---|
| | | | Time 0 | 14 days | 30 days | Time 0 | 14 days | 30 days | Time 0 | 14 days | 30 days |
| Appearance | Visual Inspection | | CCP* | CCP | CCP | CCP | CCP | CCP | CCP | CCP | CCP |
| Purity | SDS-PAGE | % Oligomer | 49% | 71% | 79% | 35% | 48% | 49% | 29% | 35% | 34% |
| | | % 16/20 kDa | 32% | 18% | 12% | 40% | 35% | 33% | 46% | 45% | 43% |
| | | % Monomer | 19% | 11% | 10% | 25% | 17% | 18% | 25% | 20% | 23% |
| Purity | SEC | % HMW | 0% | 0.4% | 0.4% | 2.9% | 3.8% | 0.5% | 14.6% | 13.4% | 17.8% |
| | | % Oligomer | 65.4% | 58.1% | 66.4% | 79.2% | 78.1% | 79.8% | 75.4% | 78.3% | 76.6% |
| | | % Monomer | 34.6% | 32.1% | 23.5% | 17.9% | 12.0% | 12.0% | 10.0% | 8.3% | 5.6% |
| | | % High Ret. Time | 0% | 9.4% | 9.7% | 0% | 6.0% | 7.7% | 0% | 0% | 0% |
| ALZ reactivity | MPD assay | Ln Excimer Gain | 0.6 | 0.6 | 0.6 | 0.5 | 0.5 | 0.4 | 0.5 | 0.5 | 0.6 |
| ThT reactivity | Fluorescence | % Aβ42 Fibril Control | 6% | 9% | 7% | 10% | 13% | 12% | 16% | 22% | 16% |

CCP = Clear, colorless, essentially free of particulate matter
HMW = High Molecular weight (i.e. elutes with excluded volume in SEC)

Example 8

Nine Month Stability Study of Lyophilized SDS Aβ Oligomers

A 9 month Aβ42 SDS oligomer stability study was conducted to compare the stability of oligomers prepared with four different dialysis buffers—(1) PSG buffer (10 mM sodium phosphate, 300 mM sucrose, 1.9% glycine), (2) PSG buffer (300 mM sucrose)/0.01% Tween20, (3) PSG 40 buffer (10 mM sodium phosphate, 40 mM sucrose, 1.9% glycine) and (4) 0.25×PBS (no sucrose). The compositions were stored lyophilized at 4° C. At time 0 and 9 months, the lyophilized samples were resuspended in 200 μL water and immediately subjected to various assays. Table 5 shows the overall results for the study.

There was no indication of sample precipitation in any samples, as determined by visual inspection.

Size Exclusion Chromatography

The four samples stored were run on an SEC column, at both time points (0 and 9 months), to determine the species A slightly different trend was seen for the oligomer composition prepared with PSG buffer containing 300 mM sucrose. The percentage of HMW species stayed substantially the same (from 0.2% to 0%), the percentage of monomer decreased by 4.7%, and the percentage of oligomer in the composition increased by a corresponding value of 4.5% (see Table 5). These results demonstrate that in PSG buffer with 300 mM sucrose, a small percentage of monomers appear to form oligomers during long-term storage. However, there is no evidence that HMW Aβ species, probable precursors to fibrillization, are being formed.

The percentage of oligomer in the composition prepared with PSG buffer/300 mM sucrose/0.01% Tween20 remained substantially the same (decreasing from 61.3% to 58.7%), as did the monomer percentage (from 38.5% to 40.2%). The percentage of HMW species increased slightly (see Table 5). Overall, these data indicate that the size profile of oligomers remain stable under these conditions, with only a nominal increase in HMW species over 9 months.

ThT Assay

Although the SEC profiles provided an indication that the soluble oligomer compositions were stable over a nine month period, the experiments do not directly indicate whether fibrillization has occurred. Therefore, the Aβ oligomer compositions were subjected to the ThT assay, as described above. As in Example 8, SDS oligomers in 0.25×PBS showed an elevated ThT response over time as compared to the PSG buffer variants, suggesting that Aβ fibrillization had occurred in these samples, as ThT binds specifically to Aβ fibrils. In contrast, the two formulation buffers containing 300 mM sucrose had background ThT fluorescence that was similar to Aβ monomer response, indicating no fibrillization. Aβ oligomers in PSG buffer (40 mM sucrose) showed a slightly higher ThT value, suggesting that some fibrillization may have occurred.

TABLE 5

Stability table of Aβ42 SDS oligomers in four formulation buffer variants:
9-month stability study under recommended storage conditions (lyophilized, 4° C.)

|  |  | PSG formulation 10 mM Na phosphate, pH 7.4 300 mM sucrose 1.9% glycine | | PSG, 300 mM sucrose + 0.01% Tween20 | | PSG (40 mM sucrose) | | 0.25X PBS | |
|---|---|---|---|---|---|---|---|---|---|
|  |  | Time 0 | 9 months | Time 0 | 9 months | Time 0 | 9 months | Time 0 | 9 months |
| Visual Inspection |  | CCP | CCP | CCP | CCP | CCP | CCP | CCP | CCP |
| SDS-PAGE | % oligomer | 68% | 66% | 64% | 62% | 63% | 63% | 62% | 59% |
|  | % monomer | 32% | 34% | 36% | 38% | 37% | 37% | 38% | 41% |
| SEC | % HMW | 0.2% | 0% | 0.2% | 1.2% | 0.2% | 3.8% | 3.3% | 18.2% |
|  | % oligomer | 50.2% | 54.9% | 61.3% | 58.7% | 73.5% | 75.5% | 77.5% | 69.1% |
|  | % monomer | 49.6% | 45.1% | 38.5% | 40.2% | 26.3% | 20.6% | 19.1% | 12.6% |
| ThT | % Aβ42 fibril ThT response | 5% | 6% | 7% | 5% | 8% | 10% | 6% | 16% |

* CCP = Clear, colorless, essentially free of particulate matter

Example 9

Characterization of Stabilized F12 Aβ42 Oligomers

Aβ oligomer compositions were prepared with F12 instead of SDS, and stabilized by a PDG buffer, as described in Example 2.

F12 Aβ oligomer compositions were prepared according to the method of Example 2, and analytically and functionally characterized, to determine the identity of each Aβ species in the compositions (i.e., monomer, oligomer, fibril).

SDS-PAGE experiments demonstrated that each F12 oligomer composition contained either 48%, 63%, 75% or 69% oligomer, depending on the lot tested (Table 6).

SEC experiments showed that each composition had a distinct oligomer species, as evidenced from the distinct elution peak in each of the F12 compositions tested (not shown). The percentage of oligomer species for each composition tested ranged from 65.9% (lot 2) to 74.1% (lot 3) (see Table 6). These results indicate, along with the SDS-PAGE data, that oligomer preparation with SDS is more reproducible than oligomer preparation with F12, and provides higher percentage oligomers, compared to the use of F12.

TABLE 6

Aβ F12 Oligomer Characterization

|  |  |  | Aβ F12 oligomers | | | |
|---|---|---|---|---|---|---|
| Test | Method |  | Lot 1 | Lot 2 | Lot 3 | Lot 4 |
| Appearance | Visual Inspection |  | CCP* | CCP | CCP | CCP |
| Concentration | BCA | mg/mL | 93 μM | 80 μM | 90 μM | 97 μM |
| Purity | SEC | % Monomer | 5.8% | 0.6% | 8.8% | 7.5% |
|  |  | % Oligomer | 70.3% | 65.9% | 74.1% | 65.8% |
|  |  | % HMV | 16.4% | 33.6% | 17.1% | 26.7% |
| Purity | RP-HPLC | % Main Peak | 78.2% | 56.8% | 69.3% | 68.2% |
| Purity | SDS-PAGE | % Monomer | 52% | 37% | 25% | 31% |
|  |  | % Oligomer | 48% | 63% | 75% | 69% |

TABLE 6-continued

Aβ F12 Oligomer Characterization

| Test | Method | | Aβ F12 oligomers | | | |
|---|---|---|---|---|---|---|
| | | | Lot 1 | Lot 2 | Lot 3 | Lot 4 |
| ALZ reactivity | MPD assay | Ln Excimer Gain (3 hr) | 1.9 | 0.5 | 0.6 | 0.7 |
| ThT reactivity | Fluorescence | % Aβ42 Fibril Control | 6% | 23% | 17% | 18% |

*Clear, colorless, free of particulate matter

Example 10

Thirty Three Day Stability Study of Aβ F12 Oligomers

Lyophilized Aβ oligomer compositions were prepared by the method of Example 2. To determine the long term stability of the preparations, the samples were resuspended in 200 μL water, and incubated at either 4° C. or 25° C., in the dark for either (1) 0 days, (2) 7 days, (3) 14 days and (4) 33 days. The "0 days" time point corresponded to the time immediately after the water resuspension step. The samples were characterized by various assays at the four time points given above. Table 7 shows the overall results from this study. The SEC data, discussed in more detail below, shows that the oligomer compositions contained substantially the same percentage of oligomer over all time points tested.

As a first measure of oligomer composition solubility, no visible particulate matter was observed at any of the time points tested.

Size Exclusion Chromatography

Figure 8:
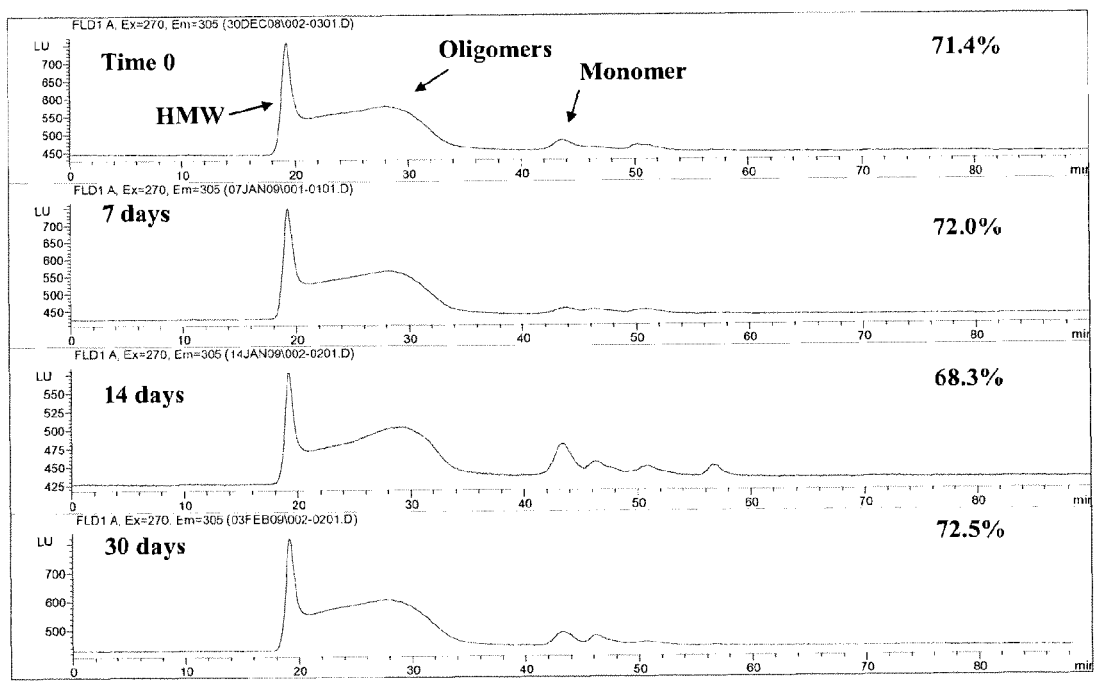
FIG. 8 shows SEC profiles of a sucrose-stabilized Aβ42 F12 oligomer, prepared with PSG buffer, at various time points (0 days, 7 days, 14 days, 33 days) after preparation and storage as a liquid at 4° C.

FIG. 8 shows the SEC profiles for the sample stored at 4° C. for each time point (i.e., 0 days, 7 days, 14 days and 33 days). It should be noted that the typical F12 SEC profile differs from SDS oligomer profiles in that there are significantly lower amounts of monomer, and increased amounts of HMW species that elute with the excluded volume (retention time=~19 minutes). Additionally, F12 oligomeric species have a higher average molecular weight than SDS oligomers described herein.

Although there was a significant proportion of HMW species at each time point, the HMW peaks overlay, which indicates no change in the amount or identity (e.g., no difference in weight, shape) of the HMW species. Therefore, it appears that PSG buffer stabilizes the preparation, as the proportion of HMW species does not increase over time (at both 4° C. and 25° C.).

Additionally, the ThT results indicate that the HMW species observed in the SEC profiles are not precursors towards Aβ fibril formation. Specifically, the overall SEC size profile appears unchanged over the time period of the study at 4° C.; whereas, the proportion of HMW species actually slightly declines over time when incubated at 25° C. Overall, the F12 SDS oligomer composition appears to be stable even under accelerated conditions when dialyzed in PSG buffer.

ThT and MPD Assays

As stated above, an increase in fluorescence in the ThT assay is directly correlated with the presence of Aβ fibrils, and Aβ oligomer instability. An increase in ThT fluorescence, indicative of an increase in fibrillization, was not observed for the sucrose stabilized F12 Aβ oligomer preparations, suggesting that the preparation remained stable for 33 days. In support of these findings, the binding observed in the MPD assay was unchanged when each sample was tested over the 33 day time period. It should be noted that the MPD assay performed for these experiments was an earlier version of the assay in which both Aβ oligomers and fibrils were reactive. Notwithstanding this fact, the ThT and MPD results, taken together, indicated that the F12 Aβ oligomer preparations remained stable, as increased fibril content and increased monomer content (dissociation) was not observed (at the 33 day time point at both 4° C. and 25° C.).

TABLE 7

Stability table of Aβ42 F12 oligomers in PSG buffer - 33 day study

| | | | 4° C. | | | | 25° C. | | | |
|---|---|---|---|---|---|---|---|---|---|---|
| | | | Time 0 | 7 days | 14 days | 33 days | Time 0 | 7 days | 14 days | 33 days |
| Visual Inspection | | | CCP | CCP | CCP | CCP | CCP | CCP | CCP | CCP |
| SDS-PAGE | % Oligomer | | 31% | 26% | 26% | 28% | 31% | 28% | 29% | 36% |
| | % 16/20 kDa | | 41% | 43% | 50% | 45% | 41% | 43% | 48% | 39% |
| | % Monomer | | 28% | 31% | 25% | 27% | 28% | 29% | 23% | 25% |
| SEC | % HMW | | 22.7% | 22.4% | 16.3% | 19.1% | 22.7% | 19.4% | 11.7% | 10.3% |
| | % Oligomer | | 71.4% | 72.0% | 68.3% | 72.5% | 71.4% | 71.5% | 68.5% | 74.2% |
| | % Monomer | | 3.9% | 3.1% | 9.8% | 4.6% | 3.9% | 2.7% | 5.5% | 2.9% |
| | % High Ret. time | | 2.0% | 2.5% | 5.6% | 3.8% | 2.0% | 6.4% | 14.3% | 12.7% |
| MPD assay | Ln Excimer Gain | | 0.5 | Not tested | 0.6 | 0.6 | 0.5 | Not tested | 0.5 | 0.5 |
| Fluorescence | % Aβ42 Fibril Control | | 16% | 15% | 16% | 11% | 16% | 11% | 17% | 12% |

CCP = Clear, colorless, essentially free of particulate matter
HMW = High Molecular Weight Patents, patent applications, publications, product descriptions, and protocols which are cited throughout this application are incorporated herein by reference in their entireties. The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A stabilized amyloid β (Aβ) oligomer composition in the form of a solution, comprising:
    soluble Aβ oligomers each comprising at least two Aβ monomer subunits in a solvent composition comprising about 10 mM phosphate, pH 7.4, 0-3% glycine and 10 mM to 400 mM of one or more disaccharides, wherein the concentration of soluble Aβ oligomers in the solution is from 8 µM to 300 µM,
    wherein said composition, if left to stand at 4° C. to 25° C. for at least one day, maintains substantially the same percentage of soluble Aβ oligomers, remains a solution with no precipitate discernible on visual inspection, and has less than 35% Aβ fiber content based on the total amount of Aβ in the composition.

2. The stabilized Aβ oligomer composition of claim 1, wherein said soluble Aβ oligomers comprise on average 2-200 Aβ subunits.

3. The stabilized Aβ oligomer composition of claim 1, wherein said one or more disaccharides is selected from the group consisting of sucrose, trehalose, and combinations of sucrose and trehalose.

4. The stabilized Aβ oligomer composition of claim 1, wherein said one or more disaccharides is selected from the group consisting of sucrose and trehalose.

5. The stabilized Aβ oligomer composition of claim 1, wherein said soluble Aβ oligomers elute as a single peak during size exclusion chromatography.

6. The stabilized Aβ oligomer composition of claim 1, wherein said composition maintains substantially the same percentage of soluble Aβ oligomers if left to stand at 4° C. to 25° C. for three days.

7. The composition of claim 1, wherein the composition has been lyophilized.

8. A lyophilized cake comprising the composition of claim 1.

9. A method for preparing a stabilized Aβ oligomer composition comprising:
    forming a SDS-Aβ oligomer solution comprising Aβ monomer peptide and 0.1% to 1.0% SDS that has no precipitate discernible on visual inspection;
    dialyzing said SDS-Aβ oligomer solution against a solution comprising a stabilizing amount of a PDG buffer to form a PDG-stabilized SDS-Aβ oligomer solution, wherein the Aβ oligomers in the solution are soluble;
    removing Aβ fibers that have formed prior to completion of said dialyzing step to form a stabilized Aβ oligomer composition.

10. The method of claim 9, further comprising isolating soluble Aβ oligomers from said stabilized Aβ oligomer composition and forming a solution of said isolated soluble Aβ oligomers, wherein the concentration of soluble Aβ oligomers in the solution is from 8 µM to 300 µM.

11. The method of claim 9, further comprising sequestering soluble Aβ oligomers from said stabilized Aβ oligomer composition and forming the stabilized Aβ oligomer composition in the form of a solution comprising:
    soluble Aβ oligomers each comprising at least two Aβ monomer subunits in a solvent composition comprising about 10 mM phosphate, pH 7.4, 0-3% glycine and 10 mM to 400 mM of one or more disaccharides, wherein the concentration of soluble Aβ oligomers in the solution is from 80 µM to 300 µM, wherein said composition, if left to stand at 4° C. to 25° C. for at least one day, maintains substantially the same percentage of soluble Aβ oligomers, remains a solution with no precipitate discernible on visual inspection, and has less than 35% Aβ fiber content based on the total amount of Aβ in the composition.

12. The method of claim 9, wherein said forming step comprises forming a SDS-Aβ oligomer solution comprising Aβ42 monomer peptide and 0.1% to 1% SDS that is substantially free of Aβ fibers.

13. The method of claim 9, wherein said forming step comprises forming a SDS-Aβ oligomer solution comprising Aβ42 and/or Aβ40 monomer peptide and 0.1% to 1% SDS and that is substantially free of Aβ fibers.

14. The method of claim 9, wherein said one or more disaccharides is selected from the group consisting of sucrose, trehalose, and combinations of sucrose and trehalose.

15. The method of claim 9, wherein the SDS-Aβ oligomer solution is formed at 37° C.

16. The method of claim 9, wherein 0.1-1.0% SDS is present in the SDS-Aβ oligomer solution.

17. A method for preparing a stabilized Aβ oligomer composition comprising:
    forming a DMEM/F12-Aβ oligomer solution comprising Aβ monomer peptide and equal parts DMEM and F12 that has no precipitate discernible on visual inspection;
    dialyzing the F12-Aβ oligomer solution against a solution comprising a stabilizing amount of a PDG buffer to form a PDG-stabilized F12-Aβ oligomer solution, wherein the Aβ oligomers in the solution are soluble;
    removing Aβ fibers that have formed prior to completion of said dialyzing step to form a stabilized Aβ oligomer composition.

18. The method of claim 17, further comprising sequestering soluble Aβ oligomers from said stabilized Aβ oligomer composition and forming a solution of said isolated soluble Aβ oligomers.

19. The method of claim 17, further comprising sequestering soluble Aβ oligomers from said stabilized Aβ oligomer composition and forming the stabilized Aβ oligomer composition in the form of a solution comprising:
    soluble Aβ oligomers each comprising at least two Aβ monomer subunits, with a solvent composition comprising about 10 mM phosphate, pH 7.4, 0-3% glycine and 10 mM to 400 mM of one or more disaccharides, wherein the concentration of Aβ oligomer in the solution is from 80 µM to 300 µM, wherein said composition, if left to stand at 4° C. to 25° C. for at least one day, maintains substantially the same percentage of soluble Aβ oligomers, remains a solution with no precipitate discernible on visual inspection, and has less than 35% Aβ fiber content based on the total amount of Aβ in the composition.

20. The method of claim 19, wherein said one or more disaccharides is selected from the group consisting of sucrose, trehalose, and combinations of sucrose and trehalose.

* * * * *